(12) United States Patent
Wester et al.

(10) Patent No.: US 8,614,290 B2
(45) Date of Patent: *Dec. 24, 2013

(54) CANCER IMAGING AND TREATMENT

(75) Inventors: Hans Jürgen Wester, Ilmmünster (DE); Horst Kessler, Garching (DE); Oliver Demmer, München (DE); Ingrid Dijkgraaf, Neubiberg (DE)

(73) Assignee: Technische Universitat Munchen, Munich (DE)

( * ) Notice: Subject to any disclaimer, the term of this patent is extended or adjusted under 35 U.S.C. 154(b) by 480 days.

This patent is subject to a terminal disclaimer.

(21) Appl. No.: 12/675,151

(22) PCT Filed: Sep. 1, 2008

(86) PCT No.: PCT/GB2008/002950
§ 371 (c)(1),
(2), (4) Date: Feb. 25, 2010

(87) PCT Pub. No.: WO2009/027706
PCT Pub. Date: Mar. 5, 2009

(65) Prior Publication Data
US 2010/0240072 A1 Sep. 23, 2010

(30) Foreign Application Priority Data
Aug. 30, 2007 (GB) .................... 0716897.4

(51) Int. Cl.
*G01N 33/567* (2006.01)
*C07K 7/64* (2006.01)

(52) U.S. Cl.
USPC ........... 530/321; 435/7.21; 435/7.1; 514/19.3

(58) Field of Classification Search
None
See application file for complete search history.

(56) References Cited

U.S. PATENT DOCUMENTS

| 2002/0106325 A1* | 8/2002 | Carpenter, Jr. ............... 424/1.69 |
| 2004/0214285 A1* | 10/2004 | Glass et al. .................... 435/69.3 |
| 2005/0265969 A1 | 12/2005 | Clark-Lewis et al. |
| 2006/0068426 A1* | 3/2006 | Tam et al. .......................... 435/6 |

FOREIGN PATENT DOCUMENTS

| JP | 2004/196769 A | 7/2004 |
| WO | WO2007/096662 A2 | 8/2007 |

OTHER PUBLICATIONS

Fujii et al. "Molecular-Size Reduction of a Potent CXCR4—Chemokine Anatagonist Using Orthogonal Combination of Conformation- and Sequence- Based Libraries" Angew Chem Int Ed Engl, 2003. 42 (28): p. 3251-3.*

Giblin et al. "Radiometallation of Receptor-specific Peptides for Diagnosis and Treatment of Human Cancer", (2005), pp. in vivo 19; 9-30.*

Fujii, N., et al., "Molecular-size reduction of a potent CXCR4-chemokine antagonist using orthogonal combination of conformation- and sequence-based libraries", Angew Chern Int Ed Engl, 2003. 42(28): p. 3251-3.

Haubner, R., et al., "Radiolabeled alpha(v)beta3 integrin antagonists: a new class of tracers for tumor targeting", J Nucl Med, 1999.40(6): p. 1061-71.

Gansbacher, B., et al., "Retroviral vector-mediated gamma-interferon gene transfer into tumor cells generates potent and long lasting antitumor immunity", Cancer Res, 1990. 50(24): p. 7820-5.

Dubridge, R.B., et al., "Analysis of mutation in human cells by using an Epstein-Barr virus shuttle system", Mol Cell Bioi, 1987.7(1): p. 379-87.

Loetscher, M., et al., "Cloning of a human seven-transmembrane domain receptor, LESTR, that is highly expressed in leukocytes", J Bioi Chern, 1994.269(1): p. 232-7.

Anton, M., et al., "Use of the norepinephrine transporter as a reporter gene for non-invasive imaging of genetically modified cells", J Gene Med, 2004. 6(1): p. 119-26.

Fan, G.H., et al., "Hsc/Hsp70 interacting protein (hip) associates with CXCR2 and regulates the receptor signaling and trafficking", J Bioi Chern, 2002. 277(8): p. 6590-7.

Forster, R., et al., "Intracellular and surface expression of the HIV-I coreceptor CXCR4/fusin on various leukocyte subsets: rapid internalization and recycling upon activation", J Immunol, 1998. 160(3): p. 1522-31.

Gupta, S.K., et al., "Pharmacological evidence for complex and multiple site interaction of CXCR4 with SDF-1 alpha: implications for development of selective CXCR4 antagonists", Immunol Lett, 2001. 78(1): p. 29-34.

Hesselgesser, J., et al., "Identification and characterization of the CXCR4 chemokine receptor in human T cell lines: ligand binding, biological activity, and HIV -1 infectivity", J Immunol, 1998. 160(2): p. 877-83.

Balkwiill, F., "Cancer and the Chemokine Network", Nature Reviews, 2004, 4: p. 540-550.

(Continued)

*Primary Examiner* — Robert A Wax
*Assistant Examiner* — Danah Al-Awadi

(57) ABSTRACT

A compound, or a pharmaceutically acceptable salt or ester thereof, comprises the structure: $[(P1-S1_j)_p-L-(S2_q-P2)_r]_t$ wherein: P1 and P2, which may be the same or different, are cyclic oligopeptide moieties, at least one of P1 and P2 having the motif B-Arg or B-(Me) Arg within the cyclic moiety, wherein B is a basic amino acid, a derivative thereof, or phenylalanine or a derivative thereof; S1 and S2 are spacer groups, which may be the same or different; L is a linker moiety containing at least two functional groups for attachment of the cyclic oligopeptides or spacer groups; n and q are independently 0 or 1; p and r are independently integers of 1 or more; and t is an integer of 1 or more, provided that, when t, p or r is greater than 1, the cyclic oligopeptide moiety, spacer group and/or the value of j or q may be the same or different between the multiple $(P1-S1_j)$ moieties or multiple $(S2_q-P2)$ moieties.

2 Claims, 6 Drawing Sheets

(56) References Cited

OTHER PUBLICATIONS

Fields GB, Noble RL, "Solid phase peptide synthesis utilizing 9-tluorenylmethoxycarbonyl amino acids", Int. J. Pept. Protein Res., 1990; 35: p. 161-214.

Biron et al., "Optimized Selective N-Methylation of Peptides on Solid Support", J.Peptide Sci. 2006; 12: p. 213-219.

Cai et al., "A thiol- reactive 18F-labeling agent, N- [2- (4-18F-fluorobenzamido)ethy I] maleimide, and synthesis of RGD peptide-based tracer for PET imaging of alpha v beta 3 integrin expression", Journal of Nuclear Medicine, Society of Nuclear Medicine, Reston, VA, US, vol. 47, No. 7, Jul. 1, 2006, pp. 1172-1180, XP002470156ISSN: 0161-5505.

Dijkgraaf et al., "Synthesis of DOTA-conjugated multivalent cyclic-RGD eptide dendrimers via 1,3- dipolar cycloaddition and their biological evaluation: implications for tumor targeting and tumor imaging purposes", Organic & Biomolecular Chemistry, Chemical Society, Letchworth., GB, vol. 5, No. 6, Mar. 21, 2007, pp. 935-944, XP002470091 ISSN: 1477-0520.

Chen et al, "Synthesis and. biological evaluation of dimeric RGD peptide-paclitaxel conjugate as a model for integrin-targeted drug-delivery", Journal of Medicinal Chemistry, American Chemical Society, Washington, US, vol. 48, No. 4, Feb. 24, 2005, pp. 1098-1106, XP002521416 ISSN: 0022-2623 [retrieved on Jan. 27, 2005].

Cheng et al., "Near- infrared fluorescent RGD peptides for optical imaging of integrin [alpha] v [beta] 3 expression in living mice", Bioconjugate Chemistry, ACS, Washington, DC, US, vol. 16, No. 6, Oct. 29, 2005, pp. 1433-1441, XP002377074 ISSN: 1043-1802.

Tamamura et al., Identification of novel low molecular weight CXCR4 antagonists by structural tuning of cyclic tetrapeptide scaffolds, Journal of Medicinal Chemistry, American Chemical Society, Washington, US, vol. 48, No. 9, May 1, 2005, pp. 3280-3289, XP002460443ISSN: 0022-2623.

Tamamura et al., "Structure- Activity Relationship Studies on CXCR4 Antagonists Having Cyclic. Pentapeptide Scaffolds" Organic & Biomolecular Chemistry, Chemical Society, Letchworth., GB, vol. 3, No. 24, Jan. 1, 2005, pp. 4392-4394, XP009082932 ISSN: 1477-0520.

Ueda et al., "Structure-Activity Relationships of Cyclic Peptide-Based Chemokine Receptor CXCR4 Antagonists: Disclosing the Importance of Side-Chain and Backbone Functionalities", J. Med. Chem., 2007, 50, pp. 192-198.

Tsutsumi et al., "Therapeutic Potential of the Chemokine Receptor CXCR4 Antagonists as Multifunctional Agents", Peptide Science, 88(2), pp. 289-289, Supplied by The British Library.

Liu, "Radiolabeled Multimeric cyclic RGD Peptides as Integrin $\alpha_v\beta_3$ Targeted Radiotracers for Tumor Imaging", Moleuclar Pharmaceutics, 3(5), pp. 472-487, Supplied by The British Library.

Thumshirn et al., "Multimeric Cyclic RGD Peptides with Improved Tumor Uptake for Tumor Targeting", American Peptide Society, 2003, pp. 693-694 Supplied by The British Library.

Wu et al., microPET of Tumor Integrin $\alpha_v\beta_3$ Expression Using $^{18}$F-Labeled PEGylated Tetrameric RGD Peptide ($^{18}$F-FPRGD4), The Journal of Nuclear Medicine, 48(9), 2007, pp. 1536-1544, Supplied by The British Library.

Chen et al., "Micro-PET Imaging of $\alpha_v\beta$-Integrin Expression with $^{18}$F-labeled Dimeric RGD Peptide", Molecular Imaging, 3(2), 2004, pp. 96-104, Supplied by The British Library.

Wu et al., "$^{18}$F-labeled mini-PEG spacered RGD dimmer ($^{18}$F-FPRGD@): synthesis and microPET imaging of $\alpha_v\beta_3$ integrin expression", Eur. J. Nucl. Med. Mol. Imaging, 2007, 34, pp. 1823-1831.

Giblin et al., "Radiometallation of Receptor-specific Peptides for Diagnosis and Treatment of Human Cancer", (2005), pp. in vivo 19; 9-30.

* cited by examiner

C

TABLE A

| Comparison of $^{125}$I-CPCR4 binding parameters | | |
|---|---|---|
| | $K_D$ [nM] | $IC_{50}$ [nM] |
| Jurkat cell (endogenous receptor expression) | 0.4 (±0.1) | 4.0 (±0.2) |
| CMS5/CXCR4 cells | 0.3 (±0.1) | 6.5 (±0.8) |
| → Identical affinity and binding behavior of $^{125}$I-CPCR4 at both cell lines | | |
| → Application of transduced CMS5/CXCR4 cells as novel tumor model | | |

D

TABLE B

Affinity profile of CXCR4 selective ligands at Jurkat and CMS5/CXCR4 cells. $^{125}$I-CPCR4 and $^{125}$I-SDF-1α were used as radioligands, respectively. Affinity was expressed as $IC_{50}$ values in nM.

| | | CPCR4 | Iodo-CPCR4 | AMD3100 | SDF-1α |
|---|---|---|---|---|---|
| $^{125}$I-CPCR4 | Jurkat | 3.7 (±0.6) | (1): 0.01 (±0.01)<br>(2): 4.6 (±0.1) | 34.2 (±18.7) | (1): 0.12 (±0.1)<br>(2): 5.4 (±1.8) |
| $^{125}$I-CPCR4 | CMS5/CXCR4 | 6.8 (±0.8) | (1): 0.01 (±0.0)<br>(2): 3.5 (±0.2) | 51.5 (±29) | (1): 0.18 (±0.2)<br>(2): 21.7 (±3.3) |
| $^{125}$I-SDF-1α | CMS5/CXCR4 | (1): 0.01 (±0.01)<br>(2): 6.9 (±4.9) | (1): 0.02 (±0.01)<br>(2): 8.8 (±6.9) | n.d. | n.d. |

FIG. 2

CANCER IMAGING AND TREATMENT

CROSS REFERENCE TO RELATED APPLICATIONS

This application is a national stage application of PCT/GB2008/002950, filed Sep. 1, 2008, which claims the benefit of UK Application No. GB 0716897.4 filed Aug. 30, 2007.

The present invention relates to the imaging and treatment of cancer. In particular, though not exclusively, it relates to compositions suitable for the targeting of radionuclides to cells expressing the chemokine receptor CXCR4 for the purposes of imaging and treatment thereof.

A method for the early assessment of the metastatic potential and metastatic spread of tumors would be a valuable tool for therapy prediction and control. Recently a key role in metastasis was attributed to the chemokine receptor CXCR4 (Müller et al. *Nature* 410 (2001) 50). In a variety of tumors such as breast and prostate cancer, CXCR4 has been found to play a dominating role during tumor cell homing and was shown to be expressed, both in primaries and metastases.

Stromal cell-derived factor 1α (SDF-1α) is the endogenous ligand for CXCR4 (Nagasawa T. et al. *PNAS.* 91 (1994) 2305). Peptide-based antagonists for CXCR4 have been described, including CPCR4 (also known as FC131, and having the sequence cyclo[D-Tyr-Arg-Arg-Nal-Gly]) (see Fujii N. et al., *Angew. Chem. Int. Ed* 42 (2003) 3251). CXCR4 is a co-receptor for HIV-1 and HIV-2, enabling entry of the viruses into cells. EP 1541585 describes radiolabeled SDF-1α for histology studies. This document also discloses a number of relatively bulky synthetic peptide antagonists of CXCR4. WO 2004/087608 discloses a CXCR4 antagonist labeled with biotin. Detection of such a compound requires the addition of a second, streptavidin-bearing reporter compound. The antagonists exemplified in WO 2004/087608 are peptides of 14 amino acids cyclised by means of a disulfide bond between Cys residues at positions 4 and 13. An Arg-Arg motif is present at positions 1 and 2, i.e. outside the cyclic moiety.

Until now, investigations with antagonists for CXCR4 (both peptide and non-peptide) have essentially been restricted to their potential use as inhibitors of the metastatic process or HIV infection. In co-pending application PCT/GB2007/000684, we describe a number of novel cyclic oligopeptide antagonists for CXCR4, and the application of CXCR4 antagonists as tracers for CXCR4 expression.

In a first aspect of the present invention, there is provided a compound, or a pharmaceutically acceptable salt or ester thereof, comprising the structure:

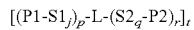

[(P1-S1$_j$)$_p$-L-(S2$_q$-P2)$_r$]$_t$ wherein:
P1 and P2, which may be the same or different, are cyclic oligopeptide moieties, at least one of P1 and P2 having the motif B-Arg or B-(Me)Arg within the cyclic moiety, wherein B is a basic amino acid, a derivative thereof, or phenylalanine or a derivative thereof;
S1 and S2 are spacer groups, which may be the same or different;
L is a linker moiety containing at least two functional groups for attachment of the cyclic oligopeptides or spacer groups;
j and q are independently 0 or 1;
p and r are independently integers of 1 or more; and
t is an integer of 1 or more,
provided that, when t, p or r is greater than 1, the cyclic oligopeptide moiety, spacer group and/or the value of j or q may be the same or different between the multiple (P1-S1$_j$) moieties or multiple (S2$_q$-P2) moieties.

The covalent linkage of two or more high affinity ligands for a receptor system using a linker or spacer group can increase the apparent binding affinity of the entire construct when compared to the monomeric ligands. When this method is used for the development of compounds or radiolabeled compounds to address the "molecular correlate" or corresponding pathways of a disease, with the aim to visualize the extent of a disease, to localize and delineate the area of the disease, or to intervene by a therapeutic strategy, higher selectivity can be reached. Thus, this methodology is a valuable improvement to monomeric ligands. The compounds of the present invention are of potential use in conditions in which the CXCR4 receptor is implicated (e.g. HIV infection, neoplastic and metastatic diseases) by virtue of their affinity for, and potential antagonism of, the receptor. Moreover, when modified to contain a detectable label, compounds of the invention may provide an efficient probe for the in vivo targeting of the CXCR4 chemokine receptor. The compounds bind with high affinity and specificity to their binding site and allow ready imaging (by a variety of methods) and hence a clear delineation of CXCR4 positive tumors (and any associated metastases) in vivo. This new class of probes/tracers may provide highly valuable tools for the investigation of the metastatic potential of tumors and early imaging, and potentially radionuclide therapy, of metastatic processes The spacer groups S1 and S2 may comprise alkyl chains of 1 to 20 carbon atoms, which may be branched or unbranched, substituted or unsubstituted, and which may be interrupted by one or more heteroatoms, cyclic groups and/or heterocyclic groups, and which have at least two functional groups suitable for attachment of the cyclic oligopeptide and the linker L. The alkyl chains of S1 and S2 may contain from 1 to 14 carbon atoms; for example, from 4 to 10 carbon atoms. The total length of the spacer groups S1 and/or S2, taking into account any interrupting heteroatoms and/or cyclic groups, may be equivalent to a linear alkyl chain of approximately 1 to 20 carbons, e.g. 1 to 14 carbons, such as 4 to 10 carbons. In certain embodiments, the spacer groups S1 and/or S2 may comprise an amino acid (or short oligopeptide chain) attached to the side group of one of the amino acids on the cyclic oligopeptide so as to branch off therefrom. For example, when B is Orn or D-Orn (or a similar basic amino acid), the spacer may comprise a glycyl group. The free amino group of the glycyl moiety is then available for attachment to the linker group L, for example when L comprises a dicarboxylic acid.

The separation between two or more monomeric ligands (the separation being made up, it will be appreciated, by the linker L and the spacer groups S1 and/or S2 when present) needs to be long enough to avoid an interference of both ligands and thus steric impairment and decrease of receptor affinity for the multimeric compound. The present inventors have surprisingly found that the optimum length of the separation to obtain high affinity for dimers and multimers is comparably small and will most probably be too short to bridge two or more receptors. Nevertheless, although "bivalent" interactions can be excluded, a significant increased affinity has been found for various multimers demonstrating the effectiveness of the present approach for the development of CXCR4 ligands. A further surprising finding is that the overall CXCR4 receptor affinity of a multimer (e.g. dimer) of cyclic oligopeptides, wherein one of the monomer oligopeptides has low or insignificant affinity for the receptor whilst the other has high affinity for the receptor, can be similar to or greater than the affinity of the 'high affinity' monomer alone. This is unexpected, since it may have been presumed that the presence of a second, non-binding oligopeptide would have reduced the ability of the high affinity peptide to bind to the receptor. This intriguing finding introduces the possibility of preparing multimers containing oligopeptides comprised of residues bearing a greater range of functional groups, thereby allowing more diverse derivatisation and functionalisation of the multimer.

At least one of P1 or P2 having the motif B-Arg or B-(Me) Arg within the cyclic moiety may have a binding affinity for the CXCR4 receptor, measured as IC50 of the corresponding monomer P1 or P2 in the presence of $^{125}$I-CPCR4, of 250 nM or lower.

The cyclic oligopeptide moiety preferably comprises 20 amino acid residues or less, more preferably 9 residues or less. In preferred embodiments, the cyclic oligopeptide is a pentapeptide. The cyclic oligopeptide is preferably cyclised via a peptide bond, which may be between its N and C termini, or may be cyclised via a disulfide bond between two cysteine residues when present. The compounds may include other moieties in addition to the cyclic oligopeptide moieties, the linker and spacers. Accordingly, additional peptide sequences may be attached, or groups capable of altering the pharmacokinetic and/or physicochemical properties of the compound (e.g. hydrophilic groups such as sugars or polyethylene glycol chains).

In certain embodiments, the oligopeptides P1 and P2 are preferably synthetic. It is currently preferred that at least one of P1 and P2 binds to CXCR4, as the corresponding monomer, with an affinity ($IC_{50}$) of 200 nM or less, more preferably 100 nM or less, and most preferably 50 nM or less. The term 'IC50' refers to the concentration of test compound required to reduce binding of the radiolabeled reference peptide $^{125}$I-CPCR4 to CXCR4-expressing cells to 50% of maximum binding. The person of ordinary skill in the art would readily be able to determine the IC50 of a given compound, and a method for doing so is described below. Compounds of the invention may bind to the CXCR4 receptor without activating the receptor (i.e. antagonist properties). Alternatively, compounds of the invention may compete with the endogenous ligand for the receptor, but activate the receptor to a lesser degree (i.e. partial agonist properties). As a further alternative, compounds of the invention may bind to the CXCR4 receptor and reduce subsequent signal transduction below the baseline, non-activated level (i.e. negative efficacy, or inverse agonist properties). In certain preferred embodiments, the compounds of the invention bind to the CXCR4 receptor without activating the receptor. In other preferred embodiments, the compounds of the invention do not comprise ligands with full agonist properties at CXCR4.

As used herein, the expression '(Me)Xaa' means an $N^\alpha$-methyl derivative of an amino acid. The expression 'Xaa (substituent)' means that the side chain of the amino acid is derivatised with the indicated substituent. The expression 'Xaa/(Me)Xaa' means that the stated amino acid may be unmethylated or may bear an $N^\alpha$-methyl group. The amino acid abbreviations used herein refer to the L-enantiomer of the respective amino acid, unless the expression 'D-Xaa' is used, in which case the D enantiomer is denoted. The term 'basic amino acid' as used herein denotes a naturally occurring or synthetic (preferably naturally occurring) amino acid having a side chain capable of receiving a proton, and becoming positively charged, under normal physiological conditions. Accordingly, basic amino acids include lysine, arginine, citrulline, ornithine, histidine, Dap (2,3-diaminopropionic acid) and Dab (2,4-diaminobutyric acid).

Preferred basic amino acids are lysine, arginine, citrulline, ornithine and histidine, more preferably arginine and ornithine.

In certain embodiments, the motif in P1 and/or P2 is B-Arg when B is a $N^\alpha$-methyl derivative of a basic amino acid. Each of P1 and P2 may have the motif B-Arg or B-(Me)Arg within the cyclic moiety.

In particular embodiments of the first aspect of the invention, at least one of P1 and P2 is selected from cyclic oligopeptides having the sequence:

cyclo[D-Tyr/(Me)D-Tyr-B-Arg/(Me)Arg-Z-(Ala)$_n$-X]

wherein:
B is as defined above, provided that the motif is B-Arg when B is a $N^\alpha$-methyl derivative of a basic amino acid;
Z is an amino acid containing an aromatic group in its side chain;
n is 1 or 0, provided that n is 1 only when the preceding four amino acids in the cyclic moiety sequence are D-Tyr/(Me)D-Tyr-Arg-Arg-Nal, Nal being L-3-(2-naphthyl)alanine; and
X is selected from Gly, (Me)Gly, Ala, Dap (diaminopropionic acid), Dap(FP) ((N-fluoropropionyl)-diaminopropionic acid), Dab (diaminobutyric acid), Dab(FP) ((N-fluoropropionyl)-diaminobutyric acid), Dab(FB) ((N-fluorobenzoyl)-diaminobutyric acid) and Dap(FB) ((N-fluorobenzoyl)-diaminopropionic acid).

Z may be selected from Nal, Dap(FB), AMS (FB) (an oxime of aminooxy serine (O-amino serine) and 4-fluorobenzaldehyde), and, when B is (Me)Arg, (Me)Nal. Z is preferably Nal.

X is preferably selected from Gly, (Me)Gly, Ala, Dap (diaminopropionic acid) and Dap(FP) ((N-fluoropropionyl)-diaminopropionic acid). X is preferably Gly or Dap(FP).

B is preferably a basic amino acid. The basic amino acid is preferably selected from Arg, Orn, D-Orn, Cit and His, Lys, Dap, Dab, or N-substituted derivatives thereof. Especially preferred are Arg, Orn, D-Orn, Cit and His, or N-substituted derivatives thereof. Most preferably, B is Arg or Orn. Ornithine residues confer the advantage of an amino-containing side chain which is relatively straightforward to derivatise. In certain embodiments, B may be $N^\alpha$-substituted with a Me group. Preferably, no more than one residue in the cyclic oligopeptide moiety is $N^\alpha$-substituted with a Me group.

When B is Orn or D-Orn, the ornithine residue may be substituted at $N^\delta$ with one or two groups which may be selected from fluorobenzoyl (FB), fluoropropionyl (FP), acetyl (Ac), amido (Am) (i.e. so as to form a urea-type moiety), methyl (Me), 1-naphthylmethyl (N1), 2-naphthylmethyl (N2), benzyl (Bz) and acyl spacer moieties. Preferably, the acyl spacer moiety is an acyl group containing a chain of 1-14 carbons, optionally interrupted by heteroatoms, and preferably having a nucleophilic functional group at its end distal to the ornithine $N^\delta$. The nucleophilic functional group may be, for example, an amino or hydroxyl group. This group enables further moieties to be added to the end of the spacer, the purpose of the spacer being to minimise the effects of any additional groups on the CXCR4 binding capability of the cyclic oligopeptide. The acyl spacer moiety may be selected from aminohexanoyl (Ahx), triethyleneglycolamino acyl (TGAS, i.e. —COCH$_2$(OCH$_2$CH$_2$)$_2$NH$_2$), (Ahx)$_2$, (Ahx)$_3$, (TGAS)$_2$ and (TGAS)$_3$. When multimers of these spacers are present, the repeating units are joined together by amide bonds. Currently preferred spacer groups are Ahx, TGAS, (Ahx)$_3$, (TGAS)$_2$ and (TGAS)$_3$. The substituents described for ornithine, including the acyl spacer moieties, may also be employed when B is Lys, Dap or Dab. In such cases, the spacer moiety preferably has a nucleophilic functional group at its end distal to its point of attachment to the oligopeptide (i.e., the N$^\epsilon$ when B is Lys). It will be appreciated that the acyl spacer moieties described above may be employed as the linker group L, or the spacer moieties S1 and/or S2, under circumstances in which the oligopeptides P1 and/or P2 are joined to the linker L or spacer S1 and/or S2 via the residue B.

In certain embodiments, B is Orn or D-Orn, preferably D-Orn, substituted at N$^\alpha$ with a Me group. When B is Orn, it may be substituted at N$^\delta$ with FB, FP, Ac, Am, N1, N2, Me and N1, Me and N2, Bz, Bz and FB, Bz and FP, Me and FB, Me and FP, or Me.

In yet other embodiments, B is Orn or D-Orn, preferably D-Orn, substituted at N$^\delta$ with FB, FP, Me and FB, or Me and FP, and optionally substituted at N$^\alpha$ with a Me group. Preferred substituents in this instance are FB, and Me and FB, optionally in conjunction with substitution of N$^\alpha$ with a Me group.

The cyclic oligopeptide moiety may have the sequence: cyclo[D-Tyr-B-Arg-Z—X], wherein B, Z and X are selected from the options listed above, provided that not more than one of the residues in the said sequence may be N$^\alpha$-methylated. Preferably in such embodiments, B is Arg. Alternatively, the cyclic oligopeptide moiety may have the sequence: cyclo[D-Tyr/(Me) D-Tyr-B-Arg/(Me)Arg-Z—X], wherein Z and X are selected from the options listed above and wherein B is selected from Arg, (Me)Arg, Orn, Cit, Orn(FB), Orn(FP), Orn(Ac), Orn(Am), Orn(N1), Orn(N2), Orn(Me, N1), Orn (Me, N2), Orn(Me), Orn(Bz), Orn(Bz,FB), Orn(Ahx), Orn (Ahx$_2$), Orn(Ahx$_3$), Orn(TGAS), Orn(TGAS$_2$), Orn (TGAS$_3$), Orn(Me,FB), D-Orn(FB), (Me)D-Orn(FB), (Me) D-Orn(Me,FB), His and Phe, provided that not more than one of the residues in the said sequence may be N$^\alpha$-methylated. In such embodiments, the first residue is preferably D-Tyr. Also in such embodiments, Z is preferably Nal. Also in such embodiments, X is preferably Gly. Also in such embodiments, the third residue is preferably Arg.

In specific preferred embodiments, at least one of the cyclic oligopeptide moieties P1 and P2 has a sequence selected from cyclo[D-Tyr-Arg-Arg-Nal-Gly]

cyclo[D-Tyr-(Me)Arg-Arg-Nal-Gly]

cyclo[D-Tyr-Arg-(Me)Arg-Nal-Gly]

cyclo[D-Tyr-Arg-Arg-Nal-(Me)Gly]

cyclo[D-Tyr-Orn-Arg-Nal-Gly]

cyclo[D-Tyr-Cit-Arg-Nal-Gly]

cyclo[D-Tyr-Arg-Arg-Nal-Ala-Gly]

cyclo[D-Tyr-Arg-Arg-Nal-Ala-Ala]

cyclo[D-Tyr-(Me)Arg-Arg-Nal-(Me)Gly]

cyclo[D-Tyr-(Me)Arg-Arg-(Me)Nal-Gly]

cyclo[(Me)D-Tyr-Arg-Arg-Nal-Ala-Gly]

cyclo[(Me)D-Tyr-Arg-Arg-Nal-Gly]

cyclo[D-Tyr-Orn(FB)-Arg-Nal-Gly]

cyclo[D-Tyr-Orn(FP)-Arg-Nal-Gly]

cyclo[D-Tyr-Orn(Ac)-Arg-Nal-Gly]

cyclo[D-Tyr-Orn(Am)-Arg-Nal-Gly]

-continued cyclo[D-Tyr-Arg-Arg-Nal-Dap(FP)]

cyclo[D-Tyr-Orn(N1)-Arg-Nal-Gly]

cyclo[D-Tyr-Orn(N2)-Arg-Nal-Gly]

cyclo[D-Tyr-Orn(Me,N1)-Arg-Nal-Gly]

cyclo[D-Tyr-Orn(Me,N2)-Arg-Nal-Gly]

cyclo[D-Tyr-Orn(Me)-Arg-Nal-Gly]

cyclo[D-Tyr-Orn(Bz)-Arg-Nal-Gly]

cyclo[D-Tyr-Orn(Bz,FB)-Arg-Nal-Gly]

cyclo[D-Tyr-Orn(Ahx)-Arg-Nal-Gly]

cyclo[D-Tyr-Orn(Ahx$_3$)-Arg-Nal-Gly]

cyclo[D-Tyr-Orn(TGAS)-Arg-Nal-Gly]

cyclo[D-Tyr-Orn(TGAS$_2$)-Arg-Nal-Gly]

cyclo[D-Tyr-Orn(TGAS$_3$)-Arg-Nal-Gly]

cyclo[D-Tyr-Orn(Me,FB)-Arg-Nal-Gly]

cyclo[D-Tyr-D-Orn(FB)-Arg-Nal-Gly]

cyclo[D-Tyr-(Me)D-Orn(FB)-Arg-Nal-Gly]

cyclo[D-Tyr-(Me)D-Orn(Me,FB)-Arg-Nal-Gly]

cyclo[D-Tyr-His-Arg-Nal-Gly]

cyclo[D-Tyr-Phe-Arg-Nal-Gly]

cyclo[D-Tyr-(Me)D-Orn-Arg-Nal-Gly]

cyclo[D-Tyr-(Me)D-Orn-Cit-Nal-Gly]

More particularly, at least one of the cyclic oligopeptide moieties P1 and P2 may have a sequence selected from:

cyclo[D-Tyr-Arg-Arg-Nal-Gly]

cyclo[D-Tyr-(Me)Arg-Arg-Nal-Gly]

cyclo[D-Tyr-Arg-(Me)Arg-Nal-Gly]

cyclo[D-Tyr-Orn-Arg-Nal-Gly]

cyclo[D-Tyr-Cit-Arg-Nal-Gly]

cyclo[D-Tyr-Orn(FB)-Arg-Nal-Gly]

cyclo[D-Tyr-Orn(FP)-Arg-Nal-Gly]

cyclo[D-Tyr-Orn(Ac)-Arg-Nal-Gly]

cyclo[D-Tyr-Orn(Am)-Arg-Nal-Gly]

cyclo[D-Tyr-Orn(N1)-Arg-Nal-Gly]

cyclo[D-Tyr-Orn(N2)-Arg-Nal-Gly]

cyclo[D-Tyr-Orn(Me,N1)-Arg-Nal-Gly]

cyclo[D-Tyr-Orn(Me,N2)-Arg-Nal-Gly]

cyclo[D-Tyr-(Me)D-Orn(FB)-Arg-Nal-Gly]

cyclo[D-Tyr-His-Arg-Nal-Gly]

cyclo[D-Tyr-(Me)D-Orn-Arg-Nal-Gly]

In particular embodiments, at least one of the cyclic oligopeptide moieties P1 and P2 has a sequence selected from either of the above lists, excluding cyclo[D-Tyr-Arg-Arg-Nal-Gly] and cyclo[D-Tyr-(Me)Arg-Arg-Nal-Gly].

In certain embodiments, at least one of the cyclic oligopeptide moieties P1 and P2 has a sequence selected from:

```
cyclo[D-Tyr-Orn-Arg-Nal-Gly]

cyclo[D-Tyr-Orn(FB)-Arg-Nal-Gly]

cyclo[D-Tyr-(Me)D-Orn(FB)-Arg-Nal-Gly]

cyclo[D-Tyr-(Me)D-Orn-Arg-Nal-Gly]
```

In preferred embodiments, the cyclic oligopeptides P1 and P2 are the same. In such embodiments, each of the cyclic oligopeptide moieties P1 and P2 may have a sequence selected from the lists given above.

In particular compounds of the invention, P1 and/or P2 have the sequence: cyclo[D-Tyr-Orn-Arg-Nal-Gly]. In other particular compounds of the invention, P1 and/or P2 have the sequence: cyclo[D-Tyr-(Me)D-Orn-Arg-Nal-Gly].

In embodiments of the first aspect of the present invention, the linker moiety L contains at least three functional groups, two of which are suitable for attachment of the cyclic oligopeptide or spacer moieties, and one of which is suitable for attachment of a detectable label or cytotoxic moiety, or a further linker moiety.

Compounds containing such 'trifiinctional' (or more highly functionalised) linkers allow the ready attachment of two oligopeptide moieties plus further groups having specific functions. For example, a third functional group on the linker L may be employed for the attachment of a cytotoxic compound for targeted chemotherapy of tumours having metastatic potential, and their associated metastases, as a result of the relatively high expression of CXCR4 by such tissues. Preferred cytotoxic moieties may be selected from any of those cytotoxic compounds generally used for chemotherapy of the tumour concerned.

Alternatively, the third functional group may be employed for attachment of a radiolabel (e.g. by means of a chelated radionuclide) for targeted radiotherapy or for diagnostic imaging. Furthermore, the additional functional groups on the linker L may be employed for the attachment of further cyclic oligopeptide moieties for increasing the affinity and specificity of the compounds. A wide variety of linkers L may be used and these may contain a large number of functional groups, for example, in the case of peptide-based functional groups. Essentially, therefore, there is no upper limit to the number of cyclic oligopeptides or spacer groups which may be joined to the linker L (i.e. the values of p and r).

Moreover, the additional functional groups on a multifunctional linker (such as a peptide) may be used for the coupling of multiple linkers, each bearing two or more cyclic oligopeptides, to each other. In this manner, higher multimers (and dendrimers) may be prepared. It will be appreciated that, in such compounds, t will be greater than 1. In certain embodiments, t may be from 1 to 100, such as 1-50, 1-30, 1-20, 1-10, 1-8 or 1-4.

In compounds of the invention, the linker moiety L may comprise a group selected from dicarboxylic acids, amino acids, linear oligopeptides, alkynes, dioximes (e.g. formed by the reaction of a dialdehyde-containing linker group and cyclic oligopeptides derivatised (e.g. at a pendant amino group) to contain one or more aminooxy groups, such as aminooxy acetyl), poly(alkylene glycols), carboxylic acid- and/or amino-substituted poly(alkylene glycols), sugars, amino-modified sugars, polyamines and oligo- or poly-aminooxy-functionalised species, such as functionalised peptides or resins. The linker may be attached to the cyclic oligopeptides using unmodified side groups of the amino acids (e.g. the pendant amino group on ornithine or lysine, or the —OH group of tyrosine), or via modified side groups (e.g. an aminooxy containing side group of e.g. lysine or ornithine). In addition, when sulphur-containing amino acids, such as cysteine, are included in the cyclic oligopeptides, the thio group can be employed for forming a thioether bond with a linker (or spacer group) containing a maleimide, alpha-haloketone or alpha-haloamide functional group. The sulphur-containing amino acids, such as cysteine, can also be modified by halogenated alkanes, with another possible functionality included therein for coupling the resulting peptide to a more complex system (e.g. bromoethylamine).

It will be appreciated that the linker L may, in certain embodiments, comprise a series of repeating units. Thus, L may comprise a short homopolypeptide, each residue of which contains functional groups for attachment of the cyclic oligopeptides or spacers, or the detectable label or cytotoxic moiety. Equally, the linker L may be made up of a series of two or more monomeric units. In the case of a linker being made up of two such monomeric units, each monomeric unit has one or more cyclic oligopeptides coupled to one or more of its functional groups, with at least one functional group of each monomeric unit, however, being joined to the other monomeric unit. In the case of a linker being made up of three of more such monomeric units, it will be appreciated that not all such units need to be joined to a cyclic oligopeptide for the overall compound to fall within the present invention. For the avoidance of doubt, it is emphasised that compounds containing linkers L made up of monomeric units, where the monomeric units may bear only one cyclic oligopeptide, but where the final compound bears two or more cyclic oligopeptides, are intended to fall within the scope of the present invention.

In preferred embodiments, the compound includes a detectable label or cytotoxic moiety. The detectable label or cytotoxic moiety may be covalently attached, directly or indirectly, to the linker moiety L. The detectable label or cytotoxic moiety may be attached to L indirectly via a spacer group S3. S3 may as defined above for S1 and S2. In particular, the label may be attached (e.g., in the case of a metal radiolabel) by means of a complexation agent which is covalently attached to a cyclic oligopeptide moiety P1 or P2 or to the linker L.

The detectable label is preferably selected from fluorescent moieties, magnetic or paramagnetic moieties, or radionuclides. For many applications, radionuclides are preferred. The label is preferably detectable without the addition of further reagents, by means of an output of detectable electromagnetic radiation or other nuclear radiation from the label itself, or as a result of its magnetic or paramagnetic properties. The label may, in some instances, be covalently bound directly to one of the cyclic oligopeptides.

When a spacer group S3 is used, as described above, the label and/or complexation agent may be attached via a nucleophilic group at the distal end of the spacer. Other intermediate groups to facilitate indirect attachment between the linker and the label would be apparent to the person of ordinary skill in the art.

The cyclic pentapeptide cyclo(D-Tyr-Arg-Arg-Nal-Gly) (also known as CPCR4 or FC131) binds to CXCR4 with high affinity. It is also relatively easy to radiolabel, e.g. by using iodine radionuclides attached to the tyrosine residue. In preliminary animal studies, radiolabeled CPCR4 showed around 10 times increased accumulation in CXCR4+ tumors compared to control tumors. The pharmacokinetic and other properties of CPCR4 may be altered by modification of the amino acid residues. In particular, N-methylation of an Arg residue, the substitution of Arg² for another cationic amino acid (e.g. ornithine), the insertion of Ala between Nal and Gly and the N-methylation of Tyr in the resulting hexapeptides all lead to modified CXCR4 antagonists maintaining useful affinity for the receptor. The dimeric or multimeric compounds of the present invention build on the above findings to produce compounds of higher affinity and higher potential specificity for the CXCR4 receptor.

In certain compounds of the invention, the radiolabel, when present, may be selected from $^{18}$F, $^{123}$I, $^{124}$I and $^{125}$I, $^{123}$I is particularly useful when the compound is to be used for in vivo single photon emission computed tomography (SPECT) studies. $^{125}$I may be preferred for in vitro or ex vivo uses of the compound. $^{18}$F and $^{124}$I are particularly useful for in vivo studies using positron emission tomography (PET) imaging.

When the compound of the invention contains one or more Dap(FB), Dap(FP), Dab(FB), Dab(FP), FB or FP groups, the fluorine substituent may be $^{18}$F. This presents a convenient means for radiolabelling such compounds. In preferred compounds of this type, the $^{18}$F is present on an FB or FP substituent at N$^δ$ of Orn or D-Orn.

Alternatively, the radiolabel may be selected from $^{211}$At, $^{225}$Ac, $^{211}$Bi and $^{212}$Bi. These radionuclides are all relatively low-range α-emitters which allow the compounds of the invention to be used for targeted radiotherapy. The low-range emission provides a safer radiotherapeutic approach for metastases. For radiotherapy of primary tumors using compounds of the present invention, it may be preferred to use a radionuclide with longer-range emission and hence, in this case, the radiolabel may be selected from beta-emitters with low and higher range, e.g. $^{177}$Lu or $^{90}$Y, $^{188}$Re and $^{131}$I, respectively.

In general, useful diagnostic isotopes (for PET and SPECT-based detection and imaging) for use in accordance with the present invention include: $^{18}$F, $^{47}$Sc, $^{51}$Cr, $^{52}$Fe, $^{52m}$Mn, $^{56}$Ni, $^{57}$Ni, $^{62}$Cu, $^{64}$Cu, $^{67}$Ga, $^{68}$Ga, $^{72}$As, $^{75}$Br, $^{76}$Br, $^{77}$Br, $^{82}$Br, $^{89}$Zr, $^{94m}$Tc, $^{97}$Ru, $^{99m}$Tc, $^{111}$In, $^{123}$I, $^{124}$I, $^{131}$I, $^{191}$Pt, $^{197}$Hg, $^{201}$Tl, $^{203}$Pb, $^{110m}$In, $^{120}$I.

In general, useful therapeutic isotopes for use in accordance with the present invention include: $^{32}$P, $^{67}$Cu, $^{77}$As, $^{90}$Y, $^{99}$Mo, $^{103}$Ru, $^{105}$Rh, $^{109}$Pd, $^{111}$Ag, $^{114m}$In, $^{117m}$Sn, $^{121}$Sn, $^{127}$Te, $^{131}$I, $^{140}$La, $^{140}$Nd, $^{142}$Pr, $^{143}$Pr, $^{149}$Tb, $^{149}$Tb, $^{149}$Pm, $^{151}$Pm, $^{153}$Sm, $^{159}$Gd, $^{161}$Tb, $^{166}$Ho, $^{166}$Dy, $^{169}$Er, $^{169}$Er, $^{169}$Yb, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{213}$Bi, $^{225}$Ac.

In certain compounds of the invention, the radiolabel is bound to the linker or a cyclic oligopeptide by means of a complex between an organic complexation agent and a radionuclide, the complex being bound to the rest of the compound in such a way as not to destroy its binding properties at the CXCR4 receptor. In such embodiments, the complexation agent is preferably covalently bound to the linker or cyclic oligopeptide (most preferably the linker), whilst the radiolabel may be covalently or non-covalently bound to the complexation agent.

The use of complexation agents broadens the range of radionuclides which may be bound to the compounds of the invention. Preferred complexation agents include DOTA (1,4,7,10-tetraazacyclododecane-N,N',N'N"-tetraacetic acid) and derivatives thereof, TETA (1,4,8,11-tetraazacyclotetradecane-1,4,8,11-tetraacetic acid), DTPA (diethylene triamine pentaacetic acid) and HYNIC (hydrazinonicotinamide). The complexation agents may be bound to appropriate side chains of the amino acids of the cyclic oligopeptides of the compounds of the invention, or to the linker group, itself generally bound to appropriate side chains of the amino acids of the cyclic oligopeptides of the compounds of the invention, i.e. so as to minimise disruption of the CXCR4-binding properties of the compound. Alternatively, intervening spacer groups S3 can be employed, as described above. In particular embodiments, amino acids (particularly synthetic amino acids) can be used as linker groups to join the complexation agent to the compounds of the invention. For example, an Ahx group can be joined to a pendant carboxylic acid group of the complexation agent (e.g. DOTA), thereby providing a distal pendant acid group for coupling to the compound of the invention, either directly or via a further group, such as an acidic amino acid, for example an aspartate group. In such a case, the remaining free diacid of the aspartate group can act as the linker L between the two cyclic oligopeptide monomers.

It is also possible to modify the compounds of the invention by the addition of one or more hydrophilic moieties (e.g. carbohydrates or polyethylene glycol chains). Such modifications can be used to improve the pharmacokinetics of the compounds in vivo. For example, a carbohydrate-modified peptide-containing compound of the invention is expected to exhibit reduced hepatic uptake and thus, compared with a lipophilic peptide, should show somewhat delayed blood clearance and predominantly renal excretion following administration. This leads to the generation of an image which is obtainable soon after administration and which is expected to be higher in contrast between CXCR4 positive and CXCR4 negative tissues.

In accordance with a fifth aspect of the invention, there is provided a pharmaceutical composition comprising a compound of the invention as described in the first, second, third or fourth aspects above, together with one or more pharmaceutically acceptable excipients. Preferably, the composition is suitable for injection.

Pharmaceutical compositions of this invention comprise any of the compounds of the present invention, or pharmaceutically acceptable salts or esters thereof, with any pharmaceutically acceptable carrier, adjuvant or vehicle. Pharmaceutically acceptable carriers, adjuvants and vehicles that may be used in the pharmaceutical compositions of this invention, depending on the intended formulation and route of administration, include, but are not limited to, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, rectally, nasally, buccally, vaginally or via an implanted reservoir. As mentioned above, parenteral administration is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques. For most applications, intravenous or intralesional (e.g. intratumoral) injection is envisaged.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol solution, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Ph. Helv, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

In accordance with a third aspect of the present invention, there is provided a method of synthesis of a compound according to the first aspect, the method comprising the combination of cyclic oligopeptides P1 and P2, linker L and, optionally, spacers S1 and/or S2, under conditions such that functional groups of the oligopeptides react with those of the linker L or, when present, those of the spacers S1 and/or S2, the other functional groups of the spacers reacting with those of the linker L.

As would be understood by the skilled person, and as suggested above, a variety of functional groups would be suitable, including amino, hydroxyl, carboxyl, acyl, amido, guanidino, thiol, alkyne, aminooxy and activated derivatives of such groups (e.g. activated esters of carboxyl groups). The skilled person would readily be able to select spacers and a linker with appropriate functional groups for attachment to the functional groups of the chosen cyclic oligopeptides. Approaches to protection and activation of the various groups on the oligopeptides would also be within his common general knowledge.

The method may further comprise the introduction of a cytotoxic moiety or detectable label, optionally bearing a spacer group S3, such that functional groups on the cytotoxic moiety or detectable label, or the spacer group S3 when present, react with functional groups on the linker L or the cyclic oligopeptide P1 and/or P2.

In preferred embodiments, the conditions used for the reaction of the cyclic oligopeptides and/or spacer groups S1 and/or S2 with the linker L are different from those used for the reaction between the cytotoxic moiety or detectable label, or spacer S3 when present, and the linker L or the cyclic oligopeptides. By selecting different functional groups for attachment of the cyclic oligopeptides or spacers S1 and/or S2, and for attachment of the cytotoxic moiety, detectable label or spacer S3, the protection and deprotection chemistry can be different for the two stages of formation of the overall construct. In other words, an orthogonal approach can be used, wherein the functional groups of the linker for attachment of the cytotoxic moiety, detectable label or S3 (or the functional groups of these components) can remain protected under conditions suitable for deprotection of the functional groups of the linker for attachment of P1, P2 or S1, S2 (or the functional groups of these components). The latter functional groups, once deprotected, can be reacted (possibly including an activation step) with P1, P2 or S1, S2 (or with the linker, where the functional groups of P1, P2, S1, S2 are the protected species requiring deprotection), without these components combining directly with the cytotoxic moiety, label or S3, and, if the linker itself contains different functional groups for attachment of the various components, potentially without attaching P1, P2, S1 or S2 to a functional group of the linker intended for attachment of the cytotoxic moiety, detectable label or S3. The skilled person would readily be able to determine suitable protection, deprotection and, if necessary, activation conditions for the functional groups. The methods of addition and removal of such protecting groups are those which would conventionally be used in relation to the particular molecule-type or group being protected, for example the methods described in standard works of reference in synthetic methodology, such as Kocienski (2004) *Protecting Groups*. 4th Edn. Georg Thieme Verlag.

In a fourth aspect, the present invention also provides a compound according to the first aspect of the invention, for use in therapy or diagnosis.

In a related aspect, the invention also provides, the use of a compound according to the first aspect of the invention in the preparation of a medicament for the treatment of a neoplastic condition. Similarly, there is also provided a compound according to the first aspect of the invention, for use in the treatment and/or diagnosis of a neoplastic condition.

By blocking CXCR4 receptors, particularly in combination with the targeting of appropriate radionuclides or cytotoxic components to CXCR4 receptor-bearing tissues, it should be possible to provide a relatively selective chemotherapy of neoplasias having metastatic potential. Any metastases or circulating tumor cells resulting from such tumors should also be targeted by the targeted radionuclide or cytotoxic component.

The invention also provides the use of a compound according to the first aspect of the invention in the preparation of a medicament for the diagnostic imaging of a neoplastic condition, the compound including a detectable label.

In certain embodiments of the uses of the compounds of the invention, the neoplasia has, or is suspected of having, metastatic potential. The neoplastic condition may, in particular, be breast or prostate cancer.

Also provided is a method of imaging neoplastic tissue, the method comprising the administration, to a subject having or suspected of having a neoplasia, of a compound according to the first aspect of the invention, and the detection of the compound following distribution thereof in vivo, the compound including a detectable label. The method may include the further step, following the detection step, of generating an image of the detected compound.

As mentioned above, the compounds of the first aspect of the invention, when bearing detectable labels, provide a highly useful tool for the selective detection and imaging of cells bearing CXCR4 receptors and hence having metastatic potential. The compounds may be administered by routine methods (e.g. i.v. injection) and images of the patient may be taken after a short time, by which stage any tissues having a relatively high expression of CXCR4 will show a relative concentration of the detectable compound of the invention.

The detection step may in particular be performed using PET or single photon emission computed tomography (SPECT) when the label is a radionuclide. When magnetic or paramagnetic labels are employed, magnetic resonance imaging is preferred.

The present invention further provides a method of determining the metastatic potential of cells of a neoplasia, the method comprising exposing the cells to a compound according to the first aspect of the invention, so as to allow the compound to bind to CXCR4 receptors on the surface of the cells, removing unbound compound from the vicinity of the cells, and determining the presence and/or amount of compound bound to the cells. The said method of determining the metastatic potential of cells may be carried out in vivo or in vitro (i.e. using a sample of cells or tissue removed from a patient).

When the method of determining the metastatic potential of cells is carried out using a compound according to the first aspect of the invention and bearing a detectable label, the imaging, or the determination of the presence and/or amount of bound compound, may in particular be performed using PET or single photon emission computed tomography (SPECT) when the label is a radionuclide. When magnetic or paramagnetic labels are employed, magnetic resonance imaging is preferred.

Other detectable labels for use in the compounds of the present invention include fluorescent components (e.g. green fluorescent protein (GFP), rhodamine).

The invention additionally provides, in yet another aspect, a method of treatment of a neoplastic condition in a subject, the neoplasia having, or being suspected of having, metastatic potential, the method comprising the administration to the subject of a compound according to the first aspect of the invention, or a composition as described above. In certain embodiments, the neoplastic condition may be breast or prostate cancer.

The invention will now be described in more detail by way of example only and with reference to the appended drawings, in which:

FIGS. 2 (A-D) illustrate the determination of $^{125}$I-CPCR4 binding parameters at CXCR4 on Jurkat cells and FIG. 2D shows the comparison thereof with $^{125}$I-SDF-Iα;

EXAMPLE 1

Figure 1:
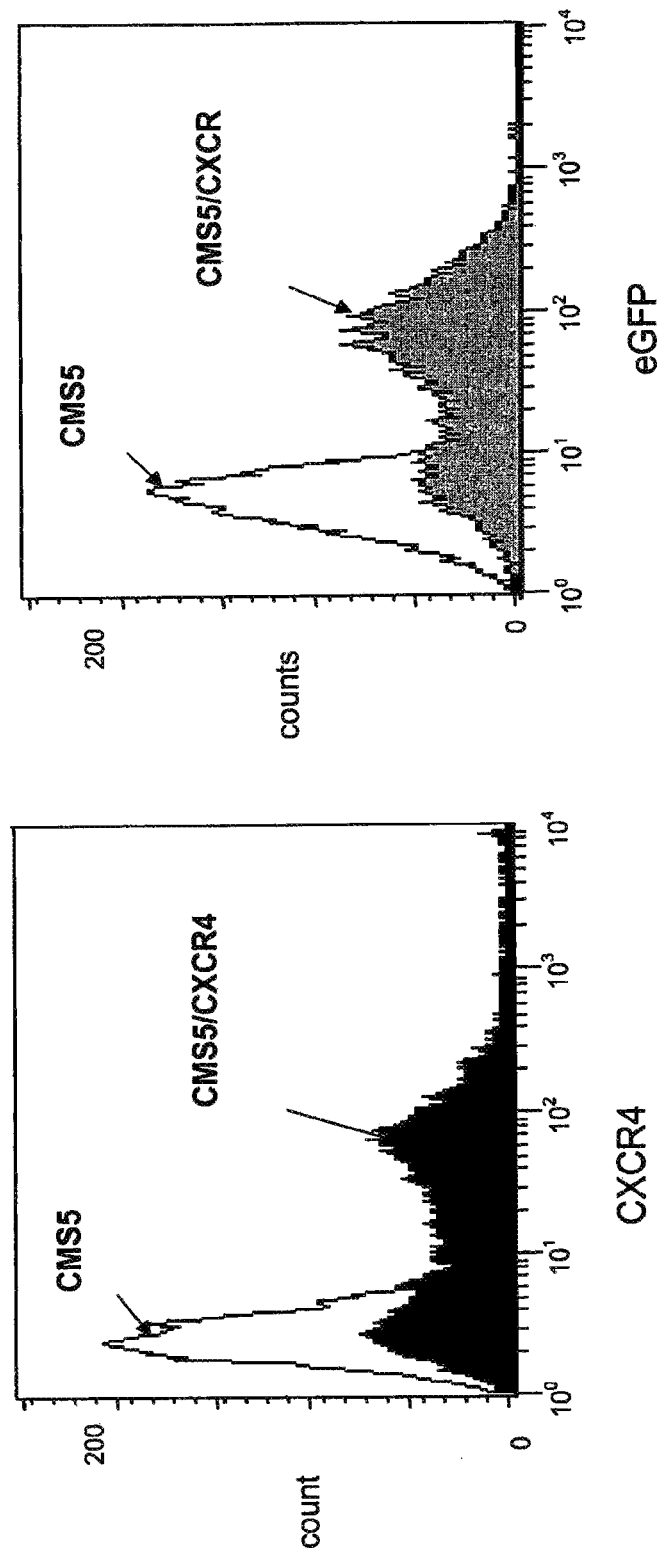
FIG. 1 shows the fluorescence-activated cell sorting (FACS) results from transfection of cells in vitro with a vector coding for CXCR4 and a GFP reporter.

Radiolabeled CPCR4SPECT/PET Imaging 1.1 Summary 1.1.1 Materials and Methods

A method for early assessment of the metastatic potential of tumors would be a valuable tool for therapy prediction and control. Recently a key role in metastasis was attributed to the chemokine receptor CXCR4. In a variety of tumors such as breast and prostate cancer, CXCR4 has been found to play a dominating role during tumor cell homing and was shown to be expressed, both in primaries and metastases. The aim of this study was to develop a novel radiolabeled probe for the in vivo imaging of CXCR4 expression on tumors and metastases by SPECT and PET imaging.

CPCR4, a cyclic peptide (cyclo(D-Tyr-Arg-Arg-Nal-Gly), was radiolabeled and evaluated in binding assays on CXCR4-expressing Jurkat cells. The tumorigenic fibrosarcoma cell line CMS5 was retrovirally transduced for stable CXCR4/GFP expression and characterized in fluorescence-activated cell sorting (FACS) and radioligand binding assays. Biodistribution studies and SPECT/PET imaging were carried out in CMS5/CXCR4$^+$ mice. Tumors were further analyzed by autoradiography, IHC and GFP fluorescence.

1.1.2 Results and Conclusions:

Radiolabeled CPCR4 binds with high affinity ($K_D$: 0.4±0.1 nM) and specificity (>90%) in an antagonistic manner to endogenously CXCR4-expressing Jurkat cells and to transduced CXCR4/GFP-expressing CMS5 cells. CMS5/CXCR4$^+$-fibrosarcomas were found to be a reliable CXCR4 tumor model in mice, as confirmed by autoradiography, immunohistochemistry (IHC) and GFP fluorescence. Biodistribution studies of i.v. injected radiolabeled CPCR4 showed 1 h post-injection 5.5±1.5% ID/g (injected dose/g) in the CMS5/CXCR4$^+$ tumor and 0.6±0.2% ID/g in the CMS5/CXCR4$^-$ control. Besides a rapid blood clearance and a low background accumulation (<1.0% ID/g) a higher tracer uptake was found in the liver 19.5±2.8% ID/g, intestine 17.2±2.9% ID/g and kidneys 12.2±2.3% ID/g. Using CPCR4-SPECT and animal PET imaging of mice, a clear delineation of CXCR4$^+$ tumors was possible, whereas no activity accumulation was visible for CXCR4$^-$ controls in the same animals.

We succeeded in the development of the first radiolabeled probe for in vivo targeting of the CXCR4 chemokine receptor. The tracer binds with high affinity and specificity in an antagonistic manner to its binding site and allowed a clear delineation of CXCR4$^+$ tumors in vivo. We hypothesize that this new class of tracers will be very promising probes for the investigation of the metastatic potential of tumors and early imaging and radionuclide therapy of metastatic processes.

Dimers and multimers of the invention, containing CPCR4 and analogues thereof as the cyclic oligopeptide moieties, are therefore of significant potential use in the treatment and imaging of metastatic processes. The binding affinity of such dimers and multimers at the CXCR4 receptor is significantly improved over the corresponding monomer oligopeptides, as shown below.

1.2 Detailed Description of Example 1

1.2.1 Materials and Methods
1.2.1.1 Peptide synthesis and radiolabeling Peptides were synthesized by using standard solid-phase peptide synthesis protocols according to the Fmoc strategy. The Fmoc amino acids Fmoc-Arg(Pbf), Fmoc-D-Tyr(tBu) and Fmoc-Gly were purchased from Novabiochem (Bad Soden, Germany), Fmoc-2-naphthylalanine was obtained from Bachem (Bubendorf, Switzerland). Peptide synthesis was performed manually on a TCP (trityl chloride polystyrene) resin. O-(1H-benzotriazol-1-yl)-N,N,N',N'-tetramethyluronium tetrafluoroborate (TBTU) and diphenyl phosphoryl azide (DPPA) were purchased from Alexis and Aldrich (Steinheim, Germany), respectively. IodoGen (1,3,4,6-tetrachloro-3R,6R-diphenylglycoluril) was obtained from Pierce (Rockford, Ill., USA), sodium iodide-125 was purchased from Hartmann-Analytic GmbH (Braunschweig, Germany) and sodium iodide-123 was obtained from Amersham Health (Eindhoven, The Netherlands). Sodium iodide-124 was kindly provided by Prof W. Brandau (Essen, Germany). All other reagents were purchased from Merck (Darmstadt, Germany) or Sigma-Aldrich (Taufkirchen, Germany). Unless specified otherwise, solvents were used without further purification.

The synthesis of the cyclic pentapeptide CPCR4 and derivatives thereof was performed as described recently with small modifications.[1, 2] In brief, after attachment of Fmoc-Gly-OH to the TCP-resin the remaining amino acids were coupled after activation with TBTU and subsequent deprotection of the Fmoc group by using 20% piperidine in DMF, respectively. After peptide chain assembly, the resin-bound peptides were treated with of a mixture of acetic acid, 2,2,2-trifluoroethanol and dichloromethane (2:2:6) for 2 h at room temperature. Afterwards the resin was filtered and washed twice with the cleavage mixture. The combined filtrates were evaporated in the presence of petrol ether in vacuum.

For cyclization the side chain protected peptides were dissolved in DMF at a concentration of 2.5 mM. At −40° C., 5 equiv. NaHCO$_3$ and 3 equiv. DPPA were added and the solution was stirred overnight with warming to room temperature. After filtration of the solid NaHCO$_3$, DMF was evaporated in vacuum. The residue was triturated with water, filtered and washed with water and diethyl ether. The fully protected cyclized peptides were treated with of a solution of 95% TFA and 5% water for 2 hours at room temperature. The deprotected peptide was precipitated from ice cold diethyl ether and centrifuged at 5° C. For the synthesis of the non-radioactive iodinated reference peptide the amino acid building block Fmoc-D-3-iodo-Tyr-OH was synthesized as described previously.[2] For the incorporation of this amino acid and subsequent peptide cyclization, PyBOP (Benzotriazol-1-yl-oxytripyrrolidinophosphonium hexafluorophosphate)/collidine activation was used. Afterwards the crude cyclic peptides were lyophilized and purified by preparative RP-HPLC. Finally, the peptides were characterized by analytical HPLC and HPLC-ESI/MS on a LCQ LC-MS system from Finnigan (Bremen, Germany) using the Hewlett-Packard series 1100 HPLC system.

Additional details of the peptide syntheses are as follows:
Materials and Methods
General All commercially available chemical reagents were used without further purification. Technical solvents were distilled before use.

Trityl resins were purchased from PepChem and amino acid derivatives from Iris Biotech GmbH, NovaBiochem, Merck, Bachem, Neosystem, Aldrich, while all other chemicals were bought from Aldrich, Fluka or Merck if not stated otherwise.

NMP (N-methylpyrrolidone) was obtained from BASF and used without further distillation. Dry solvents were purchased from Aldrich, Fluka or Merck. Dry dichloromethane was distilled from calcium hydride under argon and kept over a 4 Å molecular sieve. Water for RP-HPLC was filtered through a 0.22 µm filter (Millipore, Millipak40).

RP-HPLC analyses were performed using an Omnicrom YMC column (4.6 mm×250 mm, 5 µm C$_{18}$, 1 mL/min). The eluent was a linear gradient from water (0.1% TFA) to acetonitrile (0.1% TFA) over 30 minutes (10% to 100%, 10% to 60%, and 20% to 50%) and detection at 220 nm and 254 nm. The retention time ($R_t$) of the analytical RP-HPLC is given in minutes with the gradient in percentage of acetonitrile. Purities were determined at 220 nm with the Unicorn software package and are given relative to their starting compound. Semi-preparative RP-HPLC was done on a Beckman System Gold equipped with high pressure module 125, UV-detector 166, and using an Omnicrom ODS-A C18 (120 Å, 5 µm, 250 mm×20 mm) column in combination with the same solvents as stated above.

NMR spectra were recorded on a Bruker Avance 250 or Bruker DMX 500 at 298K. The chemical shifts are reported in ppm on the δ scale relative to the solvent signal used. $^{13}$C-NMR-spectra were recorded using $^1$H-broad band decoupling. Pulse programs were taken from the Bruker library or developed by the inventors. Samples were prepared in tubes with a diameter of 5 mm using 0.5 ml of deuterated solvent. The resulting spectra were processed on a PC workstation using Bruker TOPSPIN 1.3 software.

ESI mass spectra were recorded on a Finnigan LCQ in combination with an Agilent/HP 1100 RP-HPLC system using an Omnicrom YMC ODS-A C18 column (120 Å, 3 µm, 125 mm×2 mm) with a flow rate of 0.2 mL/min. The eluent was a linear gradient (10% to 100% acetonitrile) from water to acetonitrile with 0.1% formic acid over 20 min with detection at 220 nm.

Loading of TCP-Resin (General Procedure)

Peptide synthesis was carried out using TCP-resin (0.9 mmol/g) following standard Fmoc-strategy [13]. Fmoc-Xaa-OH (1.2 eq.) were attached to the TCP resin with DIEA (diisopropylethylamine) (2.5 eq.) in anhydrous DCM (0.8 ml/g resin) at room temperature for 1 h. The remaining trityl chloride groups were capped by addition of a solution of MeOH, DIEA (5:1; v:v) for 15 min. The resin was filtered and washed thoroughly with DCM (5×) and MeOH (3×). The loading capacity was determined by weight after drying the resin under vacuum and ranged from 0.4-0.9 mmol/g.

On-Resin Fmoc Deprotection (General Procedure)

The resin-bound Fmoc peptide was treated with 20% piperidine in NMP (v/v) for 10 minutes and a second time for 5 minutes. The resin was washed with NMP (5×).

TBTU/HOBt Coupling (General Procedure)

A solution of Fmoc-Xaa-OH (2 eq.), TBTU (2 eq.), HOBt (hydroxybenzotriazole) (2 eq.), DIEA (5.2 eq.) in NMP (1 ml/g resin) was added to the resin-bound free amine peptide and shaken for 60 min at room temperature and washed with NMP (5×).

o-Nitrobenzenesulfonyl (o-Ns) Protection

N-alkylation was carried out using an optimized protocol [14]. A solution of o-Nitrobenzenelsulfonyl chloride (o-Ns-Cl) (5 eq.) and collidine (10 eq.) in NMP (1 ml/g resin) was added to the resin-bound free amine peptide and shaken for 15 min at room temperature. The resin was washed with NMP (3×) and dry THF (3×).

N-Alkylation Under Mitsunobu Conditions

A solution of triphenylphosphine (5 eq.), DIAD (diisopropyl azodicarboxylate) (5 eq.) and alcohol ROH (10 eq.) in dry THF (1 ml/g resin) was added to the resin-bound o-Ns-protected peptides and shaken for 10 min at room temperature. The resin was filtered off, and washed with dry THF (3×) and NMP (3×).

On-Resin o-Ns Deprotection

For o-Ns deprotection, the resin-bound o-Ns-peptides were treated with a solution of mercaptoethanol (10 eq.) and DBU (5 eq.) in NMP (1 ml/g resin) for 5 minutes. The deprotection procedure was repeated one more time and the resin was washed with NMP (5×).

HATU/HOAt Coupling (General Procedure)

A solution of Fmoc-Xaa-OH (2 eq.), HATU (2 eq.), HOAt (hydroxyazobenzotriazole) (2 eq.), DIEA (4 eq.) in NMP (1 ml/g resin) was added to the resin-bound peptides and shaken for 3 hours at room temperature and washed with NMP (5×).

Alloc and Allyl Deprotection

Pd(PPh$_3$)$_4$ (0.125 eq.) in dry DCM (0.5 ml/g resin) was added to the resin-bound Alloc peptide followed by an addition of phenylsilan in dry DCM (0.5 ml/g resin) and shaken for 1 hour. The resin was washed 5 times with DCM.

On-Resin Dde Deprotection

For Dde-group deprotection, the resin-bound peptides were shaken in a solution of 2% hydrazine in NMP (1 ml/g resin) for 5 minutes. The deprotection procedure was repeated one more time and the resin was washed 5 times with NMP.

On-Resin Dde Deprotection in Presence of Alloc Protection Group

For Dde-group deprotection, the resin-bound peptides were shaken in a solution of 6.5% hydrazine in NMP (1 ml/g resin) with 200 eq. of allylic alcohol for 5 minutes. The deprotection procedure was repeated one more time for 10 minutes and the resin was washed 5 times with NMP.

Peptide Cleavage

For complete cleavage from the resin the peptides were treated three times with a solution of DCM and HFIP (4:1; v:v) at room temperature for half an hour and the solvent evaporated under reduced pressure.

Cyclization

To a solution of peptide in DMF (1 mM peptide concentration) and NaHCO$_3$ (5 eq.) DPPA (3 eq.) was added at RT and stirred over night or until no linear peptide could be observed by ESI-MS. The solvent was evaporated to a small volume under reduced pressure and the peptides precipitated in saturated NaCl solution and washed two times in HPLC grade water.

Acylation in Solution

Fully deprotected peptides were stirred with HATU (1.1 eq.) and DIEA (2.2 eq.) and the corresponding acid (1 eq.) in DMF (10 mM peptide concentration) for 30 minutes at RT. The solution was directly purified by HPLC separation.

Oxime Ligation

Fully deprotected peptides were stirred in water (pH 1-2; TFA; 10 mM peptide concentration) with the corresponding carbonyl (1 eq.) for 30 minutes at RT. The solution was directly purified by HPLC separation.

Fmoc Deprotection in Solution

The cyclic peptide was treated with 2.5 ml 20% piperidine in DMF (v/v) for 30 min and precipitated in saturated NaCl solution and washed two times in HPLC grade water.

o-Ns Deprotection in Solution

For o-Ns deprotection cyclized peptides were treated with a solution of mercaptoethanol (10 eq.) and DBU (5 eq.) in 2.5 ml DMF for 30 minutes and precipitated in saturated NaCl solution and washed two times in HPLC grade water.

Dde Deprotection in Solution

For Dde-group deprotection, the peptides were stirred in a solution of 2% hydrazine in DMF for 15-30 minutes and precipitated in saturated NaCl solution and washed two times in HPLC grade water.

Removal of Acid Labile Side Chain Protecting Groups

Cyclized peptides were stirred in a solution of TFA, water and TIPS (95:2.5:2.5) at room temperature for one hour or until no more protected peptide could be observed by ESI-MS and precipitated in diethylether and washed two more times.

Removal of DOTA t-Bu Groups

To the coupling solution with the dimerized peptides the same volume of conc. HCl was added on an ice bath under vigorous stirring. The deprotection was carried out at RT and monitored for completeness by ESI-MS every 30 min and stopped by neutralizing with conc. NH$_4$OH on an ice-bath.

Chelation of In with DOTA Ligands

DOTA ligands were dissolved in 5 M NH$_4$Cl (0.5 ml; pH 4.5) and treated with 1 nCl$_3$ (5 eq.) dissolved in 5 M NH$_4$Cl (0.05 ml). After 15 min of stirring at RT the solution was subjected to HPLC purification.

Amino Acid Synthesis

N$^\alpha$-Alloc-N$^\delta$-Boc-L-ornithine and N$^\alpha$-Alloc-N$^\delta$-Boc-D-ornithine

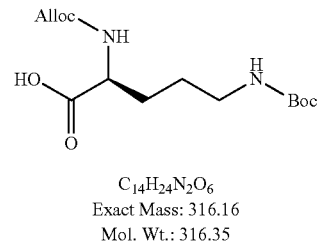

C$_{14}$H$_{24}$N$_2$O$_6$
Exact Mass: 316.16
Mol. Wt.: 316.35

N$^\epsilon$-Boc-L-ornithine (1.00 g, 4.3 mmol) was dissolved in a solution of Na$_2$CO$_3$ (1.14 g, 10.75 mmol) in water and THF (50 ml, 1:1, v/v). After addition of allyl chloroformate (0.46 ml, 4.3 mmol) the solution was stirred for 1.5 h. The THF was evaporated under reduced pressure and the aqueous phase washed with diethylether (1×50 mL), acidified with conc. HCl to pH 1 and the product extracted with EtOAc (3×50 mL). The combined organic layers were dried (Na$_2$SO$_4$), filtered, concentrated and dried in vacuo to give a colourless, sticky oil as sufficiently pure product (1.20 g, 90%). $^1$H NMR (250 MHz, DMSO-d$_6$): δ 12.52 (s, 1H, OH), 7.49 (d, 7.72 Hz, 1H, NH$^\alpha$), 6.78 (t, 5.05 Hz, 1H, NH$^\epsilon$), 5.91 (br m, 1H, CH$^{Alloc}$), 5.30 (dd, 17.15 Hz, 1.69 Hz, H$^{AllocTerm1}$), 5.19 (dd, 10.17 Hz, 1.68 Hz, H$^{AllocTerm2}$), 4.48 (m, 2H, CH$_2^{Alloc}$), 3.91 (br m, 1H, H$^\alpha$), 2.91 (m, 2H, H$^\beta$), 1.81-1.40 (br m, 4H, H$^\gamma$, H$^\delta$), 1.38 (s, 9H, H$^{BOC}$). $^{13}$C NMR (63 MHz, DMSO-d$_6$):

174.4, 156.5, 156.1, 134.1, 117.4, 77.9, 65.1, 60.2, 54.1, 28.8, 26.7, 14.6. $R_t$ (10-100%): 16.7 min.

$N^\alpha$-Alloc-$N^\epsilon$-Fmoc-L-ornithine and $N^\alpha$-Alloc-$N^\delta$-Fmoc-D-ornithine

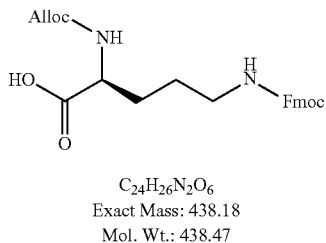

C$_{24}$H$_{26}$N$_2$O$_6$
Exact Mass: 438.18
Mol. Wt.: 438.47

$N^\alpha$-Alloc-$N^\epsilon$-Boc-L-ornithine (1.20 g, 3.87 mmol) was dissolved in DCM (10 mL) and TFA (5 mL) was added slowly. After stirring for 45 min the liquid was evaporated.

The crude product was dissolved in a solution of Na$_2$CO$_3$ (1.02 g, 9.68 mmol) in water and THF (40 ml, 1:1, v/v). After addition of FmocONsuccinimid (1.31 g, 3.87 mmol) the solution was stirred for 1.5 h. The THF was evaporated under reduced pressure and the aqueous phase washed with diethylether (1×50 mL), acidified with conc. HCl to pH 1 and the product extracted with EtOAc (3×50 mL). The combined organic layers were dried (Na$_2$SO$_4$), filtered, concentrated and dried in vacuo to give a colourless syrup as sufficiently pure product (1.65 g, 97%). $^1$H NMR (500 MHz, DMSO-d$_6$): δ 12.5 (s, 1H), 7.9 (d, 2H), 7.7 (d, 2H), 7.5 (d, 1H), 7.4 (t, 2H), 7.32 (t, 2H), 7.28 (m, 1H), 5.9 (m, 1H), 5.3 (d, 1H), 5.2 (d, 1H), 4.5 (d, 2H), 4.3 (d, 2H), 4.2 (t, 1H), 3.9 (m, 1H), 3.0 (d, 2H), 1.7 (m, 1H), 1.5 (m, 3H). $^{13}$C NMR (125 MHz, DMSO-d$_6$): 174, 156.0, 155.9, 144, 141, 133, 128, 127.0, 126.9, 125.1, 125.0, 120.1, 119.9, 65, 64, 53.54, 53.50, 47, 28, 26. $R_t$ (10-100%): 21.9 min.

The reaction scheme is shown below:

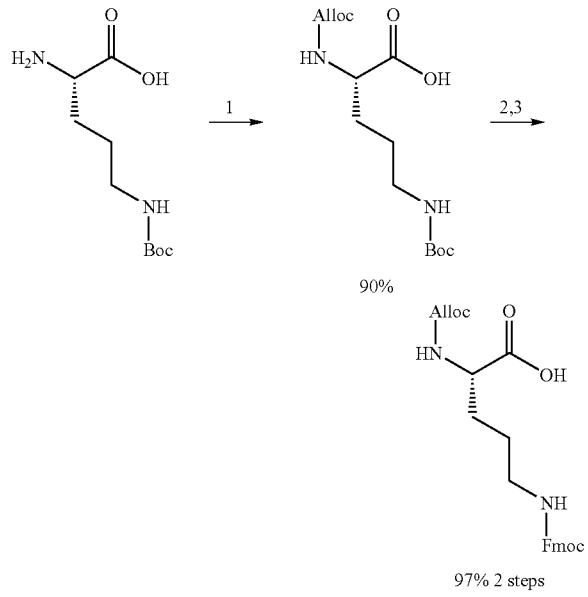

Synthesis of Glutaric Acid Mono Amide (Sodium Salt)

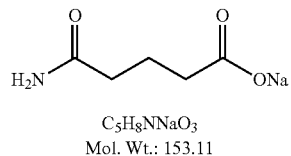

C$_5$H$_8$NNaO$_3$
Mol. Wt.: 153.11

Glutaric anhydride (0.50 g; 4.4 mmol) was dissolved in DCM (10 ml) and insoluble glutaric acid filtered off. Aqueous ammonium hydroxide was heated to 70° C. and the gas bubbled through the stirred DCM solution. After precipitation of a white solid the ammonia was heated for another 30 minutes and the DCM solution stirred over night. The white solid was filtered, washed two times with DCM (10 ml) and dried to yield 0.58 g (3.9 mmol; 89%) of glutaric acid mono amide ammonium salt.

The ammonium salt was dissolved in water (10 ml) and treated with an equimolar amount of sodium hydroxide (0.16 g) and lyophilized to yield the sodium salt.

$^1$H NMR (250 MHz, DMSO-d$_6$): δ 7.31 (s, 1H), 6.63 (s, 1H), 2.03 (q, 4H), 1.65 (m, 2H).

Synthesis of 1,4,7-Tris(tert-butoxycarbonylmethyl)-1,4,7,10-tetraazacyclododecane Hydrobromide Salt [1.HBr]

Adapted from JACS, 2008, 130, 794-795. Further analytical data can be found therein.

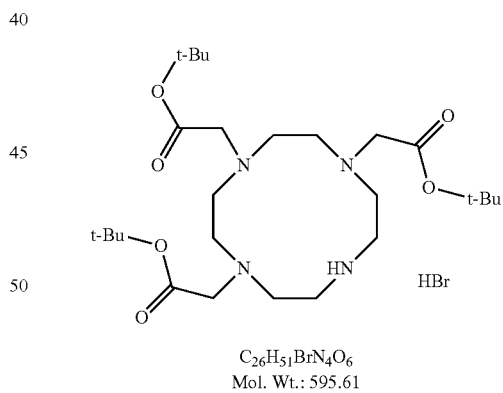

C$_{26}$H$_{51}$BrN$_4$O$_6$
Mol. Wt.: 595.61

1,4,7,10-Tetraazacyclododecane (2 g; 12 mmol; 1 eq.) and NaHCO$_3$ (5 g; 60 mmol: 5 eq.) were stirred in acetonitrile (80 ml) at 0° C. under Ar, then tert-butyl bromoacetate (5 ml; 34 mmol; 2.9 eq.) was added dropwise over a time period of 30 min. The reaction mixture was allowed to reach RT and stirred under Ar for 24 h. The inorganic solid was removed by filtration and the filtrate was evaporated under reduced pressure leaving a beige solid residue. Recrystallization from toluene (10-15 ml) afforded 1.HBr as a white solid (2.86 g; 4.8 mmol; 41% yield).

Synthesis of 1,4,7-Tris(tert-butoxycarbonylmethyl)-10-(benzyloxycarbonylmethyl)-1,4,7,10-tetraazacyclododecane [2]

Adapted from JACS, 2008, 130, 794-795. Further analytical data can be found therein.

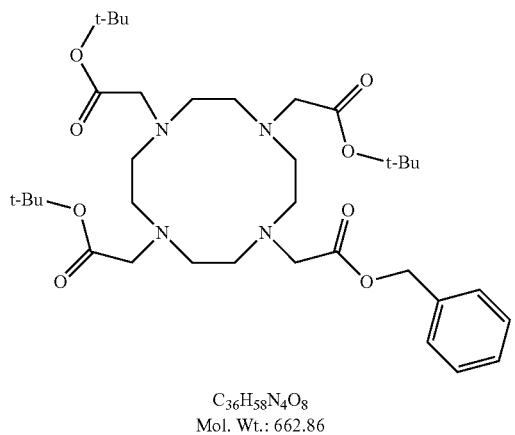 [SMILES: CC(C)(C)OC(=O)CN1CCN(CC(=O)OCc2ccccc2)CCN(CC(=O)OC(C)(C)C)CCN(CC(=O)OC(C)(C)C)CC1]

C$_{36}$H$_{58}$N$_4$O$_8$
Mol. Wt.: 662.86

To the acetonitrile solution (114 ml) of 1.HBr (2.86; 4.8 mmol; 1 eq.), were added NaHCO$_3$ (2.02 g; 24 mmol; 5 eq.) and benzyl bromoacetate (0.97 ml; 6.29 mmol; 1.3 eq.). The mixture was refluxed at 100° C. for 30 h. The reaction mixture was cooled and then filtered. The filtrate was evaporated under reduced pressure to leave a yellow gum. The product was dissolved in DCM, the purified with silica gel chromatography, eluted with 5% MeOH/DCM (R$_f$: 0.08-0.06) to yield 2 (3.15 g; 4.8 mmol; 99% yield)

Synthesis of 1,4,7-Tris(tert-butoxycarbonylmethyl)-1,4,7,10-tetraazacyclododecane-10-acetic Acid [3]

Adapted from JACS, 2008, 130, 794-795. Further analytical data can be found therein.

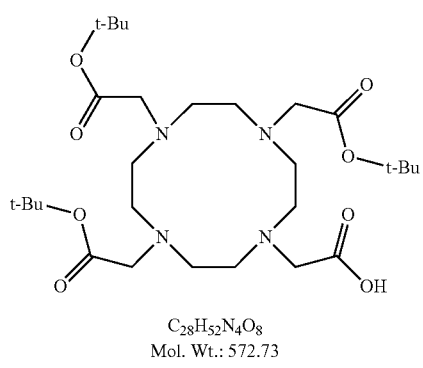 [SMILES: CC(C)(C)OC(=O)CN1CCN(CC(=O)O)CCN(CC(=O)OC(C)(C)C)CCN(CC(=O)OC(C)(C)C)CC1]

C$_{28}$H$_{52}$N$_4$O$_8$
Mol. Wt.: 572.73

Compound 2 (2.81 g; 4.2 mmol; 1 eq.) was dissolved in MeOH (110 ml), and 10% Pd/C (110 mg) was added. The reaction mixture was vigorously stirred under H$_2$ at RT for 5 h. The reaction mixture was filtered and the filtrate was evaporated under reduced pressure to afford 3 (2.23 g; 3.9 mmol; 93% yield).

Synthesis of (9H-fluoren-9-yl)methyl (R)-1-(carbonyl)-3-(tert-butoxycarbonyl)propan-2-ylcarbamate [4]

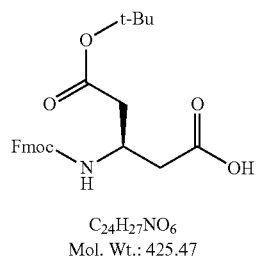

C$_{24}$H$_{27}$NO$_6$
Mol. Wt.: 425.47

N$^\alpha$-Fmoc-L-aspartic acid(tBu)OH (2.0 g; 4.9 mmol; 1 eq.) was dissolved in anhydrous THF (20 ml). Net$_3$ (0.74 ml; 5.4 mmol; 1.1 eq.) and ethylchloroformate (0.52 ml; 5.4 mmol; 1.1 eq.) were added sequentially at −15° C. Stirring was continued for 15 min and then the solution was allowed to warm up to 0° C. In the mean time N-methylnitrosourea (2.5 g; 24.3 mmol; 5 eq.) is stirred in ice-cold Et$_2$O (20 ml) and 40% KOH (20 ml; ice-cold) is added dropwise until complete dissolution. The yellow diazomethane solution in Et$_2$O was added dropwise at 0° C. to the amino acid solution and it was then allowed to warm up to RT and stirred for another 2.5 hours. Excess diazomethane was decomposed by dropwise addition of HOAc. The solution was washed with sat. NaHCO$_3$, sat. NH$_4$Cl, and brine. The organic layer was dried (Na$_2$SO$_4$) and evaporated under reduced pressure. The resulting diazo ketone was dissolved in water/dioxane (1:5; v/v; 160 ml). After addition of silver benzoate (0.12 g; 0.5 mmol; 0.1 eq.) the mixture was sonicated in an ultrasound bath until complete conversion (30 min) monitored by TLC (MeOH/DCM; 1:20; R$_f$: 0.1-0.2). After evaporation of dioxane under reduced pressure the solution was acidified with 5% HCl and the precipitate extracted with EtOAc (three times). The organic layer was dried (Na$_2$SO$_4$) and evaporated under reduced pressure and the crude product purified by flash chromatography (MeOH/DCM; 1:20; R$_f$: 0.1-0.2) to yield [4] (1.3 g; 3.1 mmol; 63% yield).

$^1$H NMR (250 MHz, DMSO-d$_6$): δ 12.2 (s, br, 1H), 7.90 (d, 2H), 7.69 (dd, 2H), 7.42 (t, 2H), 7.33 (m, 3H), 4.27 (m, 3H), 3.59 (m, 1H), 2.41 (m, 4H), 1.38 (s, 9H), $^{13}$C NMR (75 MHz, DMSO-d$_6$): 172.49, 170.24, 144.35, 141.19, 128.07, 127.51, 125.63, 120.56, 80.39, 65.80, 60.20, 47.17, 45.81, 28.13. R$_t$ (10-100%): 23.5 min. ESI (m+Na): 448.1.

Synthesis of (9H-fluoren-9-yl)methyl (R)-1-((allyloxy)carbonyl)-3-(tert-butoxycarbonyl)propan-2-ylcarbamate [5]

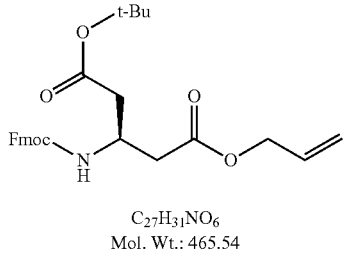

C$_{27}$H$_{31}$NO$_6$
Mol. Wt.: 465.54

[4] (0.98 g; 2.3 mmol; 1 eq.) was stirred with allyl bromide (5.52 ml; 6.4 mmol; 2.8 eq.) and DIEA (0.78 ml; 4.6 mmol; 2 eq.) in ACN (4.6 ml) at 45° C. for 1 h. The reaction was monitored by TLC MeOH/DCM (1:20; v/v). The solution was allowed to reach RT. After addition of EE (20 ml) the organic layer was washed with sat. KHSO$_4$, sat. NaHCO$_3$, and half sat. NaCl, dried (Na$_2$SO$_4$), and evaporated under reduced pressure to yield [5] (0.77 g; 1.7 mmol; 74% yield).

$^1$H NMR (250 MHz, CDCl$_3$): δ 7.76 (d, 2H), 7.58 (d, 2H), 7.40 (t, 2H), 7.31 (m, 2H), 5.91 (m, 1H), 5.63 (d, 1H), 5.32 (m, 1H), 5.24 (d, 1H), 4.60 (d, 2H), 4.36 (m, 3H), 4.21 (m, 1H), 2.66 (m, 4H), 1.45 (s, 9H), $^{13}$C NMR (75 MHz, CDCl$_3$): 143.91, 141.29, 131.84, 127.67, 127.04, 125.08, 119.95, 118.57, 66.86, 65.38, 47.21, 45.13, 39.26, 38.08, 28.05. R$_t$ (10-100%): 27.6 min. ESI (m+Na): 488.3.

Synthesis of (9H-fluoren-9-yl)methyl (S)-1-((allyloxy)carbonyl)-3-(carbonyl)propan-2-ylcarbamate [6]

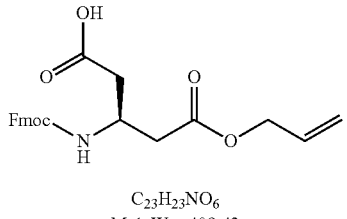

C$_{23}$H$_{23}$NO$_6$
Mol. Wt.: 409.43

[5] (0.77 g; 1.65 mmol) was dissolved in DCM (4 ml) and TFA (2 ml) was added and stirred for 2 h at RT. After evaporation to dryness the solid was dissolved in sat. NaHCO$_3$, washed with ether, acidified (pH 2) with HCl (5%) to form a white precipitate that was extracted two times with EE. The organic layer was washed with acidified water (HCl, pH 1), dried (Na$_2$SO$_4$) and evaporated under reduced pressure to yield [6] (0.58 g; 1.4 mmol; 85% yield)

$^1$H NMR (250 MHz, CDCl$_3$): δ 7.75 (d, 2H), 7.68 (s, 1H), 7.57 (d, 2H), 7.40 (t, 2H), 7.31 (m, 2H), 5.89 (m, 1H), 5.66 (d, 1H), 5.28 (m, 2H), 4.60 (d, 2H), 4.38 (m, br, 2H), 4.22 (m, 1H), 2.62 (m, 4H), $^{13}$C NMR (75 MHz, CDCl$_3$): 143.69, 141.33, 131.60, 127.77, 127.10, 125.00 120.01, 118.87, 67.25, 65.65, 47.13, 44.47, 37.87, 37.64. R$_t$ (10-100%): 22.0 min. ESI (m+Na): 432.2.

Synthesis of N$^α$-Fmoc-L-aspartic Acid (t-Bu) Allylester [7]

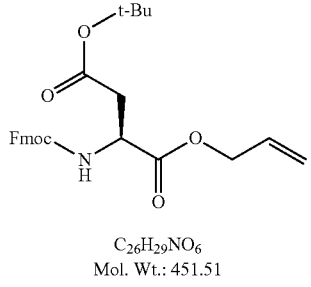

C$_{26}$H$_{29}$NO$_6$
Mol. Wt.: 451.51

N$^α$-Fmoc-L-aspartic acid (β-t-Bu ester) (0103 g; 2.50 mmol; 1 eq.) was stirred with allyl bromide (6.0 ml; 7.0 mmol; 2.8 eq.) and DIEA (0.78 ml; 5.0 mmol; 2 eq.) in ACN (5.0 ml) at 45° C. for 100 min. The reaction was monitored by TLC MeOH/DCM (1:20; v/v). The solution was allowed to reach RT. After addition of EE (40 ml) the organic layer was washed with sat. KHSO$_4$, sat. NaHCO$_3$, and half sat. NaCl, dried (Na$_2$SO$_4$), and evaporated under reduced pressure to yield [8] (1.01 g; 2.24 mmol; 90% yield).

$^1$H NMR (250 MHz, CDCl$_3$): δ 7.74 (d, 2H), 7.58 (m, 2H), 7.38 (t, 2H), 7.29 (t, 2H), 5.89 (m, 1H), 5.81 (d, 1H), 5.32 (d, 1H), 5.23 (d, 1H), 4.56 (m, 3H), 4.37 (m, 3H), 4.23 (m, 1H), 2.86 (m, 2H), 1.42 (s, 9H), $^{13}$C NMR (75 MHz, CDCl$_3$): 170.62, 170.00, 155.98, 143.91, 143.73, 141.29, 131.49, 127.71, 127.07, 125.13, 119.98, 118.80, 81.89, 67.28, 66.30, 50.61, 47.10, 37.79, 28.03. R$_t$ (10-100%): 27.8 min. ESI (m+Na): 474.3.

Synthesis of N$^α$-Fmoc-L-aspartic Acid (OH) Allylester [8]

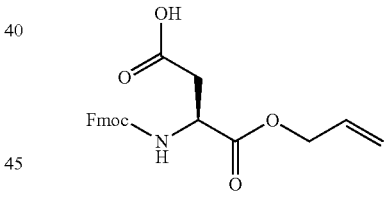

C$_{22}$H$_{21}$NO$_6$
Mol. Wt.: 395.41

[7] (1.01 g; 2.23 mmol) was dissolved in DCM (4 ml) and TFA (2 ml) was added and stirred for 1 h at RT. After evaporation to dryness the solid was dissolved in sat. NaHCO$_3$, washed with ether, acidified (pH 2) with HCl (5%) to form a white precipitate that was extracted two times with EE. The organic layer was washed with acidified water (HCl, pH 1), dried (Na$_2$SO$_4$) and evaporated under reduced pressure to yield [8] (0.77 g; 1.94 mmol; 87% yield)

$^1$H NMR (250 MHz, DMSO): δ 7.90 (m, 2H), 7.83 (m, 1H), 7.70 (d, 2H), 7.42 (m, 2H), 7.32 (m, 2H), 5.87 (m, 1H), 5.30 (d, 1H), 5.18 (m, 1H), 4.58 (d, 2H), 4.45 (m, 1H), 4.26 (m, 3H), 2.70 (m, 2H), $^{13}$C NMR (75 MHz, CDCl$_3$): 171.85, 171.29, 144.22, 141.20, 132.72, 128.11, 127.540, 125.66 120.59, 118.03, 66.24, 65.52, 51.02, 47.07, 36.32. R$_t$ (10-100%): 22.0 min. ESI (m+Na): 418.1.

Synthesis of 3tBuDOTA-Ahx-Asp [9]

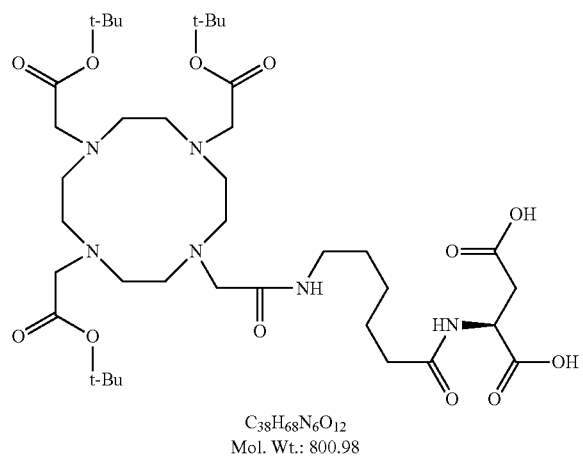 [SMILES: CC(C)(C)OC(=O)CN1CCN(CC(=O)NCCCCCC(=O)N[C@@H](CC(=O)O)C(=O)O)CCN(CC(=O)OC(C)(C)C)CCN(CC(=O)OC(C)(C)C)CC1]

$C_{38}H_{68}N_6O_{12}$
Mol. Wt.: 800.98

[9] was synthesized on solid support using [3], [8], and Fmoc-6-aminocapronic-1-acid and purified by HPLC.

HPLC-MS: $R_t$=8.37 min; m/z (m+H)=801.4

3tBuDOTA-Ahx-betaAsp [10]

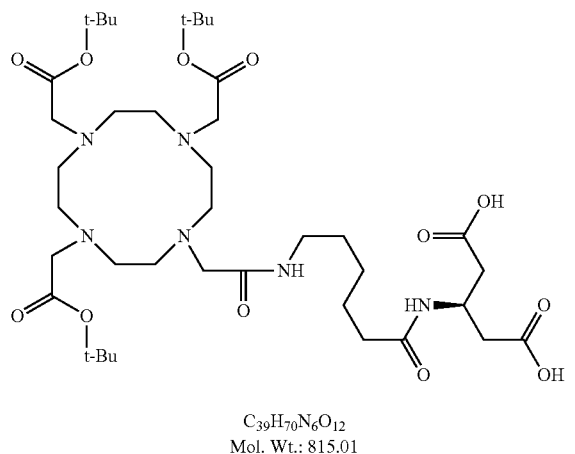

$C_{39}H_{70}N_6O_{12}$
Mol. Wt.: 815.01

[10] was synthesized on solid support using [3], [6], and Fmoc-6-aminocapronic-1-acid and purified by HPLC.

HPLC-MS: $R_t$=8.29 min; m/z (m+H)=815.4

In order to attach the above DOTA derivatives to the oligopeptide groups, the above approach 'Acylation in Solution' was employed.

1.2.1.2 Peptide Radioiodination

CPCR4 was labeled with $^{123}$I, [124]I or $^{125}$I-iodide using the Iodogen method.[2] 0.2 mg of the peptide were dissolved in 250 µl phosphate buffered saline (PBS, pH 7.4). This solution was added to Eppendorf cups coated with 150 µg Iodogen and was combined with the radioiodide solution. After 15 min at room temperature, the solution was removed from the solid oxidizing reagent. Purification was performed using gradient RP-HPLC. Radiochemical purity was generally >95%. For animal experiments the fraction containing the radiolabeled peptide was diluted with water and bound to a Sep-Pak C18 column. Afterwards the column was washed with water and the radiolabeled peptide was eluted with methanol. After removal of the methanol in vacuum the residue was dissolved and diluted in PBS (pH 7.4). For storage at 4° C. the solution was acidified with 0.1% trifluoroacetic acid in $H_2O$ containing 20% ethanol.

1.2.1.3 Lipophilicity

For the determination of the lipophilicity 0.4-2.7 µCi of $^{125}$I-CPCR4 in 500 µl PBS (pH 7.4) was mixed with 500 µl octanol and was vigorously vortexed. After centrifugation for quantitative phase separation, 100 µl from each phase were withdrawn and radioactivity was determined in a gamma counter. The experiment was performed in triplicates and repeated two times independently.

1.2.1.4 Cell Lines and Tissue Culture

The murine fibrosarcoma cell line CMS5[3] and the human 293T cell line[4] (kindly provided by R. Willemsen, Department of Clinical and Tumour Immunology, Daniel den Hoed Cancer Center, Rotterdam, The Netherlands) were both cultured in Dulbeccos's modified Eagle's medium, supplemented with 10% (v/v) fetal calf serum (PAA, Linz, Austria) and 1% (v/v) L-glutamine. The T-lymphocyte Jurkat cell line (ATCC) was maintained in RPMI 1640 medium supplemented with 10% (v/v) fetal calf serum (FCS) and 1% (v/v) L-glutamine. Media and supplements were obtained from Biochrom (Berlin, Germany), unless otherwise mentioned.

1.2.1.5 Construction of the Retroviral Vector and Target Cell Transduction

The cDNA coding for enhanced fluorescence protein was excised from pEGFP (BD Biosciences Clontech, Germany) by NcoI StuI digest, blunt ended using Klenow enzyme and inserted into the unique SmaI site of pIRESneo3 (BD Biosciences Clontech, Germany) to obtain pIRESeGFPneo3. In the next step the Nod fragment carrying IRES-eGFP was cloned into the NotI site of pBullet (Schaff et al. 2003) to obtain pBulletIRESeGFP. The 1292 bp HindIII XbaI fragment of pcDNA3CXCR4[5] carrying the human chemokine receptor type 4 (CXCR4) cDNA (kindly provided by B. Moser, Bern) was isolated and cloned into the BamHI site of the retroviral vector pBulletIRESeGFP after blunt ending all sites with Klenow enzyme. The resulting vector was designated pBulletCXCR4-IRES-eGFP. Retrovirus production by transient transfection of 293T cells and transduction of CMS5 cells have been described elsewhere.[6]

1.2.1.6 FACS Sorting and Analyses

EGFP and CXCR4 expression of trypsinized cells was analyzed with a fluorescence activated cell sorter (Becton Dickinson FACS Vantage, Heidelberg, Germany) using Argon Laser beam (Spectra-Physics) of excitation energy 40 mW at 488 nm and the CellQuest Software. EGFP expression was measured directly, using FL1 (530/30 nm) filter. Dead cells were determined by addition of propidium iodide to the cells and fluorescence was determined using a FL2 585/42 nm filter. The percentage of dead cells was always 0.2%. The population of CXCR4 expressing CMS5 cells was enriched by sorting CXCR4-EGFP-co-expressing cells for FL1 with a minimum fluorescence of 20.

CXCR4 expression on the cell surface of trypsinized cells was determined using a phycoerythrine (PE)-labeled monoclonal rat antibody with specificity for human CXCR4 (1D9, BD Biosciences Pharmingen, Heidelberg, Germany). Trypsinized cells were washed with FACS buffer (PBS, 0.5% FCS) and $1\times10^6$ cells were stained with 0.5 $_L$ μg antibody for 30 min. in the dark at 4° C. Cells were extensively washed with ice-cold FACS buffer and analyzed by flow cytometry. Nonspecific staining was assessed by PE-conjugated rat $IgG_{2b,\kappa}$ (BD Biosciences Pharmingen, Heidelberg, Germany). Detection of CXCR4 on the cell surface was in the same samples as EGFP and was detected using a 575/26 nm filter (FL2). CXCR-4 staining was plotted against EGFP fluorescence (FL1).

Where indicated cells were resuspended in medium supplemented with 0.5% bovine serum albumin (BSA) (Sigma, Tauflcirchen, Germany), incubated with recombinant human 100 nM SDF-1α (R&D Systems, Wiesbaden, Germany) for 1 hr at 37° C. (adapted from protocols published previously)[7, 8]; controls were incubated with diluent (PBS/0.1% BSA). Samples were immediately transferred to ice to avoid further internalization, centrifuged, washed with PBS/0.5% BSA and FACS staining for CXCR4 was performed as indicated above.

1.2.1.7 Receptor Binding Assays

For receptor binding assays cells were resuspended in PBS/0.2% BSA. A total of 200 μl of the suspension containing 400,000 Jurkat cells were incubated with 25 μl of the tracer solution (containing 3.1 kBq, approx. 0.1 nM) and 25 μl of the diluent or the competitor at different concentrations. For determination of $IC_{50}$ values, cyclo(D-Tyr$^1$[$^{125}$I]-Arg$^2$-Arg$^3$-Nal$^4$-Gly$^5$) was used as a tracer. Nonspecific binding was determined in the presence of 1 μM cold cyclo(D-Tyr$^1$[$^{127}$I]-Arg$^2$-Arg$^3$-Nal$^4$-Gly$^5$). After shaking for 2 h at room temperature, the incubation was terminated by centrifugation at 1300 rpm for 5 min. Cell pellets were washed once with cold PBS followed by a second centrifugation step. Cell bound radioactivity was determined by using a gamma counter. Experiments were repeated 2-3 times in triplicates. $IC_{50}$ values of the compounds were calculated by nonlinear regression using GraphPad Prism (GraphPad Prism 4.0 Software, Inc., San Diego, Calif., USA). Each data point is the average of three determinations.

1.2.1.8 In Vivo Studies

For animal experiments parental CMS5 cells and transduced CMS5/CXCR4 cells were injected subcutaneously in female Swiss nu/nu mice (Charles River, France). Therefore for each mouse $1.5\times10^6$ CMS5 cells and $2\times10^6$ CMS5/CXCR4 cells were resuspended in 75 μl PBS, respectively and mixed with the same volume Matrigel-Matrix HC (BD Biosciences, Heidelberg, Germany) according to the manufacturer's protocol. Subsequently cell suspension was inoculated at each shoulder, respectively. After 14-16 days of tumour growth mice were used for imaging and biodistribution purposes. All animal experiments were approved by the local authorities and are in compliance with the institutions guidelines.

1.2.1.9 Biodistribution Studies 370 kBq (10 μCi) of $^{125}$I-labeled CPCR4 were injected intravenously into the tail vain of tumour bearing mice. The animals were sacrificed and dissected 30, 60 and 120 min after tracer injection. Organs of interest were removed and the radioactivity was measured in weighted tissue samples using the 1480 Wizard3 gamma counter from Wallac (Turku, Finland). Results are expressed as percent injected dose per gram tissue weight (% ID/g). Each value represents the mean of four to six animals.

1.2.2 Results 1.2.2.1 CPCR4-Synthesis and Radiolabeling

The synthesis of CPCR4, the cyclic pentapeptide cyclo(D-Tyr-Arg-Arg-Nal-Gly) that shows high affinity and selectivity for the CXCR4 receptor, was carried out by using standard Fmoc solid phase peptide synthesis protocols on an acid labile tritylchloride resin as described previously.[1, 2] Additional modifications by N-alkylation were done using a modified protocol designed for N-methylation via a Fukuyama-Mitsunobu reaction. [14] After peptide chain assembly the side chain protected peptide was cleaved from the resin and was cyclized using the DPPA method.[2] After removal of all protecting groups the crude cyclic pentapeptide was further purified by preparative HPLC. Analytical HPLC and HPLC/ESI-MS analyses proved homogeneity and identity of the peptides.

The radiolabeling at the Tyr side chain of CPCR4 was performed either with $^{123}$I- or $^{125}$I-iodide using the Iodogen method and subsequent separation of the unlabeled precursor by HPLC. The HPLC conditions applied allowed very efficient separation of the radioiodinated peptide from the unlabeled precursor and side products thus resulting in high radiochemical purity (>99%) and specific activity. The specific activity of the labeled peptides was assumed to be that of the radioiodide used for labeling (>2000 Ci/mmol for $^{125}$I, >5000 Ci/mmol for $^{123}$I). Whereas the radioiodide incorporation was usually >95%, the overall radiochemical yield of the $^{123}$I- and $^{125}$I-labeled peptides after HPLC purification and biocompatible formulation was in the range of 50%. After biocompatible formulation in PBS the lipophilicity of $^{125}$I-CPCR4 was determined as octanol/water(PBS) partition coefficient. A logP value of -0.04 (±0.01) was obtained.

1.2.2.2 CXCR4-Vector Construction and Viral Infection

The mouse fibrosarcoma cell line CMS5 was retrovirally transduced with CXCR4-IRES-eGFP. In the cell pool 70-80% of the retrovirally CXCR4-transduced CMS5 cells were positive for eGFP-expression as determined by FACS analysis with a mean fluorescence intensity of 130. Growth curves and survival assay (XTT) demonstrated that both cell lines had similar growth kinetics in vitro (data not shown). When CMS5 cells and CMS5/CXCR4 cells were stained for human CXCR4, CMS5 showed a background staining of 2.2% whereas 61.6% of CMS5/CXCR4 cells stained positive for human CXCR4, exhibiting a mean fluorescence intensity of 66 and 57.9% of the cells were positive for both CXCR4 and eGFP. (FIG. 1) The cell line was stable over time as indicated by repeated FACS analyses (data not shown).

1.2.2.3 Receptor Binding Studies

The suitability of $^{125}$I-CPCR4 as a CXCR4-radioligand was tested first at Jurkat cells that endogenously express the CXCR4 receptor [9, 10] and subsequently at CMS5/CXCR4 cells that were retrovirally transduced for CXCR4 expression. For both cell lines reproducible high specific binding was found by using $^{125}$I-SDF-1α (50-70%) and $^{125}$I-CPCR4 (>90%). At parental CMS5 cells both tracers showed negligible binding in the range of the non-specific binding of Jurkat and transduced CMS5/CXCR4 cells. From saturation binding curves nearly identical $K_D$ values in the sub-nanomolar range (0.3 to 0.4 nM) were obtained for both cell lines indicating high affinity of $^{125}$I-CPCR4 for the CXCR4 receptor. (FIG. 2 and associated Table A) Furthermore a high number of $^{125}$I-CPCR4 binding sites (Bmax) was determined. Whereas for Jurkat cells the Bmax value was more dependent on origin and varies stronger with culture conditions, the number of binding sites (Bmax) on CMS5/CXCR4 cells was constant and better reproducible (23±6 fmol receptor protein).

Figure 2:
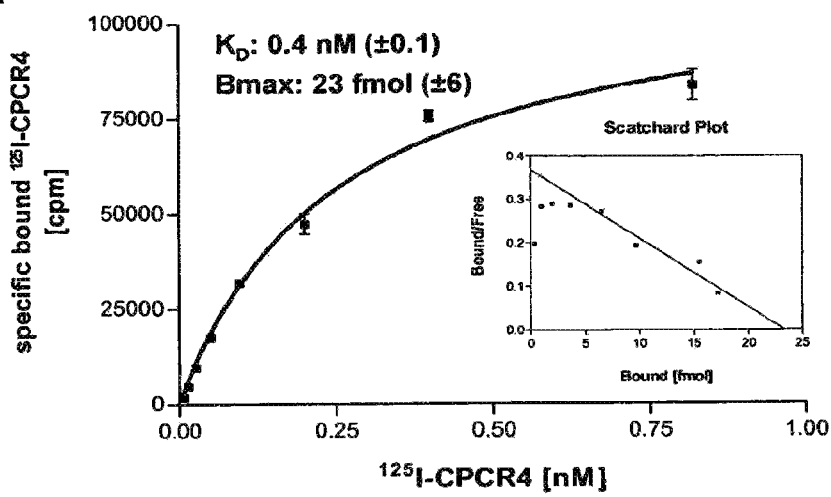
Figure 2:
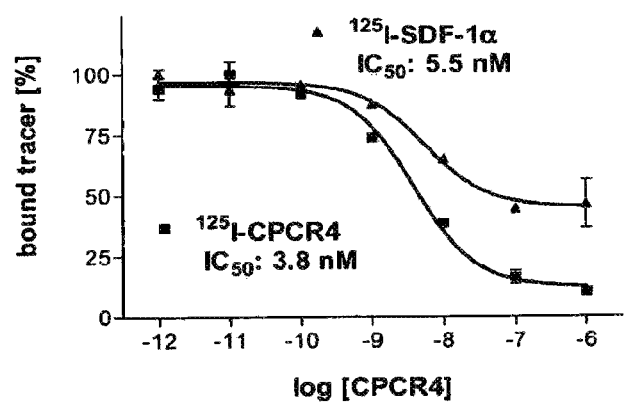

With $^{125}$I-CPCR4 as novel radioligand the affinity profile of distinct CXCR4 selective ligands was ascertained in competitive radioligand binding assays. (FIG. 2, Table B) For SDF-1α, CPCR4 and its non-radioactive iodinated reference compound Iodo-CPCR4 high affinities with nanomolar $IC_{50}$ values were found either with $^{125}$I-CPCR4 or $^{125}$I-SDF-1α at the CXCR4 receptor. In comparison with SDF-1α and the cyclic pentapeptides the CXCR4 selective bicyclam AMD3100 showed reduced affinity with both tracers. Depending on tracer and competitor two CXCR4 binding sites were monitored as reported previously.[9] For analysis of the binding curves one-site and two-site competition curve fits were used as required. The resulting high and low affinity binding sites were designated as (1) and (2). (FIG. 2, Table B).

The receptor internalization after binding of $^{125}$I-CPCR4 at the CXCR4 receptor was analyzed after two short washing steps with an acidic buffer (pH5.0). Thereafter the tracer was mostly releasable from the receptor (>80%). This indicates that no receptor internalization occurs as expected from a receptor antagonist (data not shown).

1.2.2.4 Receptor Functionality

To determine whether the human CXCR4 is functional in mouse cells, cells were pre-incubated with human SDF-1α, stained for surface CXCR4 and subsequently FACS analysis was performed. 54.7% of CMS5/CXCR4 cells stained positive for CXCR4 after pre-incubation with human SDF-1α as compared to 79.2% of control-treated cells, indicating functionality of the human receptor in murine CMS5 cells. The CXCR4-background staining in CMS5 cells decreased from 7.9 to 2.7% in the presence of SDF-1α. Jurkat cells served as positive control and did not exhibit a decrease in % positive cells, but a drop in mean fluorescence intensity from 385.4 to 155.4. In CMS5/CXCR4 cells the mean fluorescence intensity did drop from 209.0 of mock treated cells to 80.5 of SFD-1α treated cells. This indicates that Jurkat cells do contain more CXCR4 receptors than CMS5/CXCR4 cells.

1.2.2.5 In Vivo Studies

Figure 3:
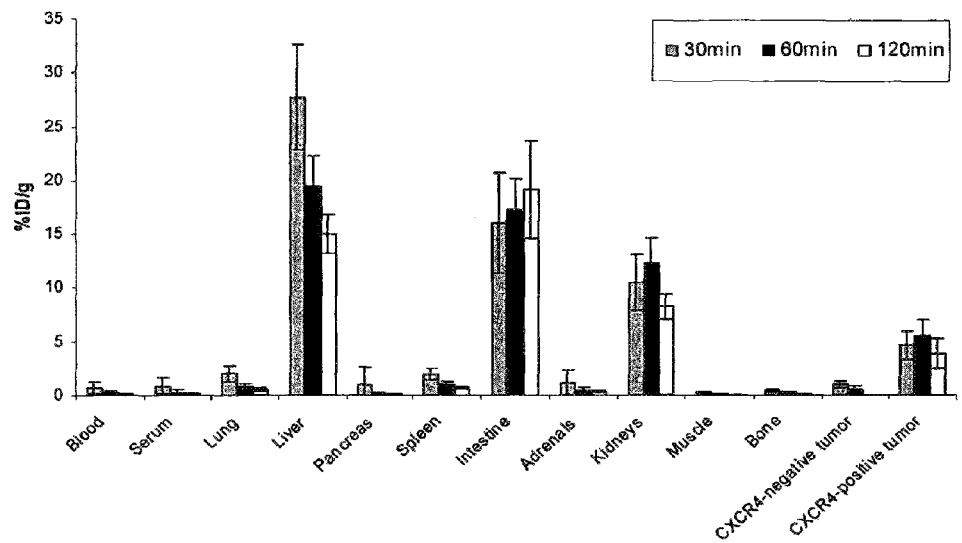
FIG. 3 (A-B) illustrates the biodistribution of 125I-CPCR4 following intravenous injection thereof in nude mice.

The biodistribution and tumour accumulation of $^{125}$I-CPCR4 was determined 30, 60 and 120 min post injection in CMS5 and CMS5/CXCR4 tumour bearing nude mice. Highest tumour accumulation of $^{125}$I-CPCR4 in CMS5/CXCR4 tumours was achieved after 60 min with 5.5 (±1.5) percent of injected dose per gram (% ID/g) whereas in parental CMS5 tumours only 0.6 (±0.2) % ID/g were observed at this time. After 30 min $^{125}$I-CPCR4 shows an accumulation in CMS5/CXCR4 tumours with 4.7 (±1.3) % ID/g and after 120 min with 3.8 (±1.4) % ID/g. For all time points a higher tracer accumulation was observed only for liver, intestine and kidneys. Other organs showed only very low background accumulation. Whereas in the liver the accumulation of $^{125}$I-CPCR4 decreases with the time from 27.7 (±4.9) % ID/g after 30 min to 15.0 (±1.8) % ID/g at 120 min, the tracer accumulation in the intestine slightly increases from 16.0 (±4.7) % ID/g after 30 min to 19.2 (±4.5) % ID/g at 120 min indicative for the metabolic processes in these organs. The tracer accumulation in the kidneys shows a peak after 60 min with 12.2 (±2.3) % ID/g and decreases to 8.2 (±1.1) % ID/g after 120 min. (FIG. 3 and table)

Figure 4:
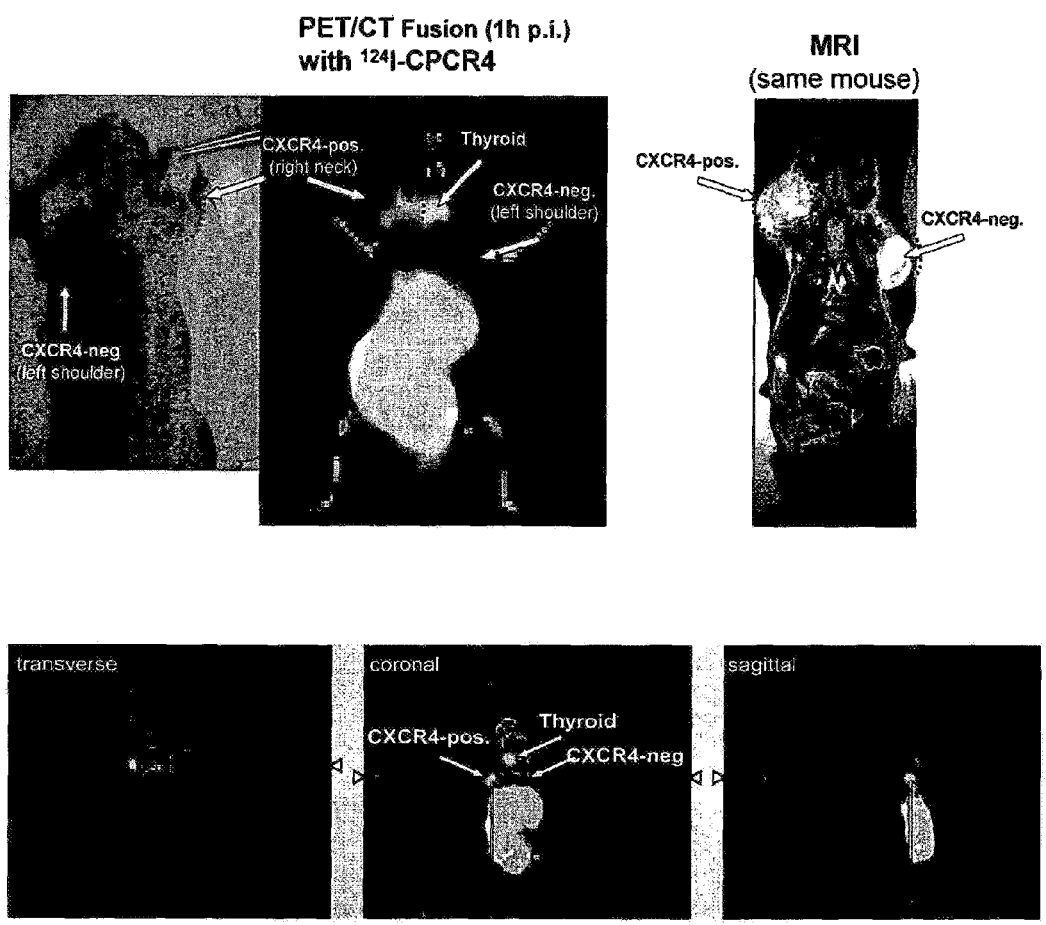
FIG. 4 shows PET/SPECT images of radiolabelled CPCR4 distribution in mice bearing CXCR4 positive and negative tumours.

FIG. 4 shows PET/SPECT results for radioiodinated-CPCR4 distribution in mice bearing both CXCR4-positive (CMS5/CXCR4) and negative (CMS5 control) tumours. A clear delineation can be observed due to the difference in CPCR4 uptake of the two types of tumour. MRI results are shown for comparison. The CXCR4 positive tumour was recognisable by PET even after 25 hr post injection. Similar results were obtained using PET with $^{18}$F-labeled radioligand, and using a gamma camera with $^{123}$I-labeling. Similarly, in ex vivo analysis of cryosections of tumours using a micro-imager, marked differences in radiation could be seen between positive and negative tumours.

EXAMPLE 2

Development of Cyclic Peptides for Targeting CXCR4Chemokine Receptor Expression

Several diseases like HIV-1 infection, cancer metastasis, rheumatoid arthritis and chronic lymphocytic B-cell leukemia are linked to the interaction of the CXCR4 chemokine receptor to its natural ligand, the 68 amino acid containing protein stromal cell-derived factor-1α (SDF-1α) [11]. One strategy for the treatment of these diseases could be to block the interaction between CXCR4 and SDF-1α with small CXCR4 antagonists. Furthermore, radiolabeling of suitable compounds with appropriate radioisotopes could provide agents for imaging of CXCR4 expression in vivo via PET.

Previous studies by Fujii et al. on CXCR4 antagonists led to the high affinity cyclic pentapeptide CPCR4, having the sequence cyclo[Gly-D-Tyr-Arg-Arg-Nal][1]. To further improve this structure, different approaches have been chosen with respect to metabolic stability, bioavailability, conformational rigidity and chemical versatility for radiolabeling.

First, an N-methyl scan of the backbone amides was performed to influence conformational freedom and to increase metabolic stability and bioavailability. $N^\alpha$-methylation of arginine residues yielded peptides with useful affinity ($IC_{50}$ values of 23 nM (N-Me)Arg$^3$ and 31 nM (N-Me)Arg$^4$, respectively, with Arg residues numbered according to their position in the sequence as set out in the preceding paragraph) whereas N-methylation of other amino acids noticeably decreased the affinity ($IC_{50}$>100 nM). By substitution of Arg$^3$ by ornithine, the affinity was mostly retained [12]. The delta-amino group of Orn can be alkylated or acylated via radiolabeled groups containing short lived isotopes. Moreover, the bioavailability should be improved as the high basicity of the two guanidino groups could be reduced. First ornithine-acylated derivatives showed $IC_{50}$ values between 11 and 35 nM enabling for the first time $^{18}$F-radiolabeling of small CXCR4 antagonists for PET imaging in vivo. The panel below shows the results obtained with cyclic Orn-containing pentapeptides in which the Orn is delta-N substituted with FB, FP, Ac and Am, respectively.

Affinities of Various CXCR4 Antagonists

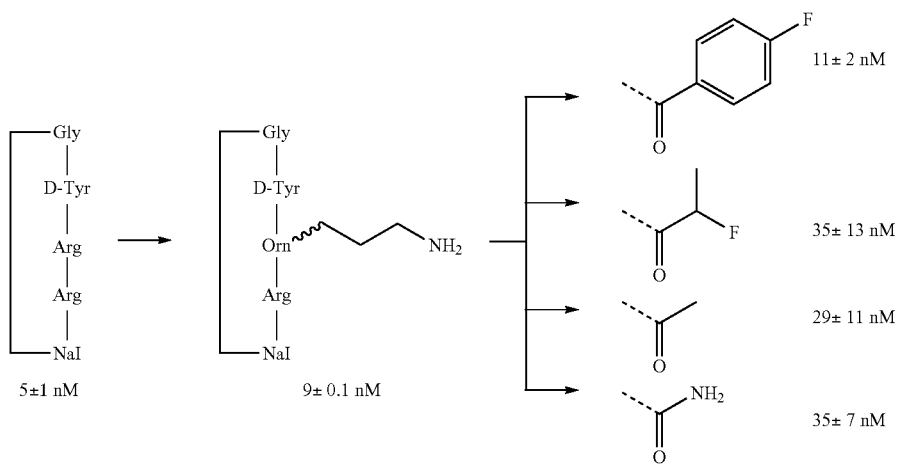

The results of binding assays with $N^\alpha$-monomethylated cyclic pentapeptides ($N^\alpha$-methyl scan) are shown in Table 1 below (note that in the following tables, peptides having $IC_{50}$ values >250 nM, and thus not falling within the first to third aspects of the present invention, are included for comparative purposes and are marked with * after the $IC_{50}$ value):

From these results, it can be observed that a loss of affinity by a factor of only 5-10 is obtained when Arg residues are methylated. A larger loss is obtained when other residues are methylated.

Corresponding results with $N^\alpha$-dimethylated pentapeptides are shown below (Table 2), indicating a further loss of affinity from such a modification:

TABLE 1

| Code | Sequence | $IC_{50}$ [nM] | Calculated mass | Observed m/z (m + H) |
|---|---|---|---|---|
| CPCR4* | cyc[D-Tyr-Arg-Arg-Nal-Gly] | 4 | | |
| OD1 | cyc[D-Tyr-(Me)Arg-Arg-Nal-Gly] | 23 | 743.39 | 744.7 |
| OD3 | cyc[D-Tyr-Arg-(Me)Arg-Nal-Gly] | 31 | 743.39 | 744.7 |
| OD5 | cyc[D-Tyr-Arg-Arg-(Me)Nal-Gly] | 894* | 743.39 | 744.7 |
| OD7 | cyc[D-Tyr-Arg-Arg-Nal-(Me)Gly] | 136 | 743.39 | 744.6 |
| OD9 | cyc[(Me)D-Tyr-Arg-Arg-Nal-Gly] | 247 | 743.39 | 744.7 |

The structure of OD1 (cyc[D-Tyr-(Me)Arg-Arg-Nal-Gly]) is as follows:

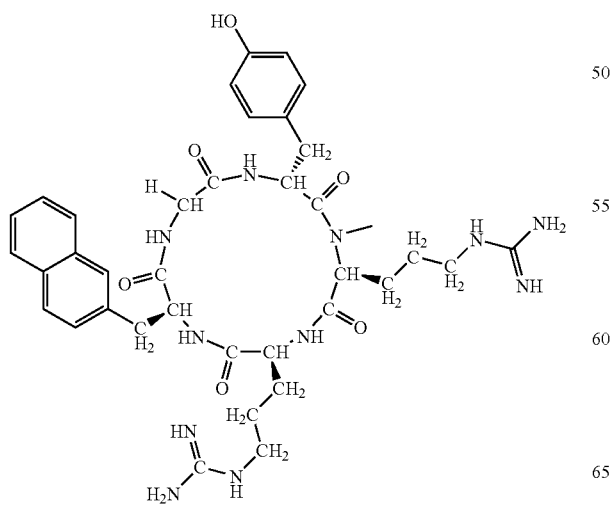

TABLE 2

| Code | Sequence | IC$_{50}$ [nM] | Calculated mass | Observed m/z (m + H) |
|---|---|---|---|---|
| OD11 | cyc[(Me)Arg-Nal-Gly-(Me)D-Tyr-Arg] | >1000* | 757.4 | 758.7 |
| OD12 | cyc[(Me)Arg-(Me)Nal-Gly-D-Tyr-Arg] | >1000* | 757.4 | 758.6 |
| OD13 | cyc[Arg-Nal-(Me)Gly-(Me)D-Tyr-Arg] | >1000* | 757.4 | 758.7 |
| OD14 | cyc[Arg-(Me)Nal-Gly-(Me)D-Tyr-Arg] | >1000* | 757.4 | 758.6 |
| OD15 | cyc[Arg-Nal-(Me)Gly-D-Tyr-(Me)Arg] | ~300-400* | 757.4 | 758.8 |
| OD16 | cyc[Arg-Nal-Gly-(Me)D-Tyr-(Me)Arg] | ~1000* | 757.4 | 758.8 |
| OD18 | cyc[Arg-(Me)Nal-(Me)Gly-D-Tyr-Arg] | >1000* | 757.4 | 758.8 |
| OD19 | cyc[(Me)Arg-Nal-(Me)Gly-D-Tyr-Arg] | >1000* | 757.4 | 758.9 |
| OD20 | cyc[Arg-(Me)Nal-Gly-D-Tyr-(Me)Arg] | 100-200 | 757.4 | 758.7 |
| OD21 | cyc[(Me)Arg-Nal-Gly-D-Tyr-(Me)Arg] | >1000* | 757.4 | 758.6 |

The results of binding assays with pentapeptides in which Arg was substituted with ornithine or citrulline are shown in Table 3 below:

TABLE 3

| Code | Sequence | IC$_{50}$ [nM] | Calculated mass | Observed m/z (m + H) |
|---|---|---|---|---|
| OD23 | cyc[Nal-Gly-D-Tyr-Orn-Orn] | >1000* | 645.33 | 646.5 |
| OD24 | cyc[Nal-Gly-D-Tyr-Arg-Orn] | ~1000* | 687.35 | 688.6 |
| OD25 | cyc[Nal-Gly-D-Tyr-Orn-Arg] | 9 ± 0.1 | 687.35 | 688.4 |
| OD26 | cyc[Nal-Gly-D-Tyr-Cit-Cit] | >1000* | 731.34 | 732.6 |
| OD27 | cyc[Nal-Gly-D-Tyr-Cit-Arg] | 35 ± 7 | 730.36 | 731.6 |
| OD28 | cyc[Nal-Gly-D-Tyr-Arg-Cit] | >1000* | 730.36 | 731.7 |

The results of Table 3 indicate that the first Arg residue in cyclic pentapeptides may be substituted with a cationic residue, such as ornithine, without dramatic loss of affinity.

In an evaluation of side chain-acylated ornithine derivatives for incorporation of $^{18}$F-containing prosthetic groups, it was found that the fluorobenzoylated derivative showed the highest affinity (11 nM—see panel above). This compound showed a relatively high lipophilicity (LogP 1.06).

A number of other Orn-N$^\delta$ and/or Orn-N$^\alpha$-modified pentapeptides were also prepared, including a series of derivatives with N$^\delta$ spacer moieties. The CXCR4 binding results are shown in Table 4.

TABLE 4

| Sequence | IC$_{50}$ [nM] | Calculated mass | Observed m/z (m + H) |
|---|---|---|---|
| cyc[D-Tyr-Orn(Me)-Arg-Nal-Gly] | 105 ± 7 | 701.36 | 702.7 |
| cyc[D-Tyr-Orn(Bz)-Arg-Nal-Gly] | 155 ± 63 | 777.4 | 778.6 |
| cyc[D-Tyr-Orn(N1)-Arg-Nal-Gly] | 40 ± 3 | 827.41 | 828.6 |
| cyc[D-Tyr-Orn(N2)-Arg-Nal-Gly] | 49 ± 1 | 827.41 | 828.7 |
| cyc[D-Tyr-Orn(Me,N1)-Arg-Nal-Gly] | 39.7 | 841.43 | 842.7 |
| cyc[D-Tyr-Orn(Me,N2)-Arg-Nal-Gly] | 34.2 | 841.43 | 842.7 |
| cyc[D-Tyr-Orn(FB)-Arg-Nal-Gly] | 11 ± 2 | 809.37 | 810.6 |
| cyc[D-Tyr-Orn(Bz,FB)-Arg-Nal-Gly] | 100 | 899.41 | 900.7 |
| cyc[D-Tyr-Orn(Me,FB)-Arg-Nal-Gly] | 78 ± 25 | 823.38 | 824.6 |

TABLE 4-continued

| Sequence | IC$_{50}$ [nM] | Calculated mass | Observed m/z (m + H) |
|---|---|---|---|
| cyc[D-Tyr-Orn(Ahx)-Arg-Nal-Gly] | 70 ± 23 | 800.43 | 801.7 |
| cyc[D-Tyr-Orn(Ahx$_2$)-Arg-Nal-Gly] | 947* | 913.51 | 914.9 |
| cyc[D-Tyr-Orn(Ahx$_3$)-Arg-Nal-Gly] | 227 | 1026.6 | 1027.9 |
| cyc[D-Tyr-Orn(TGAS)-Arg-Nal-Gly] | 125 | 832.42 | 833.7 |
| cyc[D-Tyr-Orn(TGAS$_2$)-Arg-Nal-Gly] | 189 | 977.49 | 978.9 |
| cyc[D-Tyr-Orn(TGAS$_3$)-Arg-Nal-Gly] | 146 | 1122.57 | 1123.9 |
| cyc[D-Tyr-Orn(Ac)-Arg-Nal-Gly] | 29 ± 11 | 729.36 | 730.6 |
| cyc[D-Tyr-Orn(Am)-Arg-Nal-Gly] | 35 ± 7 | 730.36 | 731.6 |
| cyc[D-Tyr-Orn(FP)-Arg-Nal-Gly] | 35 ± 13 | 761.37 | 762.6 |
| cyc[D-Tyr-Orn(Palm)-Arg-Nal-Gly] | >1000* | 925.58 | 926.9 |

In addition, a series of pentapeptides containing derivatives of D-Orn were prepared, together with pentapeptides in which B is His or Phe. The CXCR4-binding results are shown in Table 5.

TABLE 5

| Sequence | IC$_{50}$ [nM] | Calculated mass | Observed m/z (m + H) |
|---|---|---|---|
| cyc[D-Tyr-D-Orn(FB)-Arg-Nal-Gly] | 86 | 809.37 | 810.6 |
| cyc[D-Tyr-(Me)D-Orn(FB)-Arg-Nal-Gly] | 8.7 ± 0.6 | 823.38 | 824.6 |
| cyc[D-Tyr-(Me)D-Orn(Me,FB)-Arg-Nal-Gly] | 59 | 837.4 | 838.6 |
| cyc[D-Tyr-His-Arg-Nal-Gly] | 30 | | |
| cyc[D-Tyr-Phe-Arg-Nal-Gly] | 154 | | |

A number of cyclic hexapeptides in which an Ala or similar residue was inserted in the chain were tested for binding affinity to CXCR4. The results are shown in Table 6 (note—Dap(FP) is (N-fluoropropionyl)-diaminopropionic acid):

TABLE 6

| Code | Sequence | IC$_{50}$ [nM] |
|---|---|---|
| CPCR4* | cyc[D-Tyr-Arg-Arg-Nal-Gly] | 4 |
| BL 36 | cyc[D-Tyr-Arg-Arg-Nal-Ala-Gly] | 75 (±7) |
| BL 56 | cyc[D-Tyr-Arg-Arg-Nal-D-Ala-Gly] | >1000* |
| BL 58 | cyc[D-Tyr-Arg-Arg-Nal-Dap(FP)-Gly] | ~1000* |
| BL 37 | cyc[D-Tyr-Arg-Arg-D-Ala-Nal-Gly] | ~1000* |
| BL 38 | cyc[D-Tyr-Arg-Arg-nal-Gly] | >1000* |
| BL 39 | cyc[D-Tyr-Arg-Arg-D-Ala-Ala-Gly] | >1000* |
| BL 40 | cyc[D-Tyr-Arg-Arg-nal-Ala-Gly] | ~1000* |
| BL 42 | cyc[D-Tyr-Arg-Arg-Nal-Nal-Gly] | >1000* |
| BL130 | cyc[D-Tyr-Arg-Arg-Nal-Gly-Gly] | ~1000* |
| BL131 | cyc[D-Tyr-Arg-Arg-Ala-Nal-Gly] | >1000* |
| BL132 | cyc[D-Tyr-Arg-Ala-Arg-Nal-Gly] | >1000* |
| BL133 | cyc[D-Tyr-Arg-D-Ala-Arg-Nal-Gly] | >1000* |
| BL134 | cyc[D-Tyr-D-Ala-Arg-Arg-Nal-Gly] | >1000* |
| BL135 | cyc[D-Tyr-Ala-Arg-Arg-Nal-Gly] | >1000* |
| BL136 | cyc[D-Ala-D-Tyr-Arg-Arg-Nal-Gly] | >1000* |
| BL137 | cyc[Ala-D-Tyr-Arg-Arg-Nal-Gly] | ~1000* |
| BL158 | cyc[D-Tyr-Arg-Arg-Nal-Ala-Ala] | 114 |

The results of Table 6 suggest that Ala may be inserted between Nal and Gly, and/or Gly may be replaced with Ala, with only moderate loss of affinity. Insertion of other residues in this position, or insertion of any of the residues studied in Table 6 in other positions, was not well tolerated.

A further N$^\alpha$-methyl scan was conducted with a series of cyclic hexapeptides (N-mono-, di- and trimethylated), as reported in Table 7:

TABLE 7

| Code | Sequence | IC$_{50}$ [nM] |
| --- | --- | --- |
| BL56 | cyc[Arg-Nal-D-Ala-Gly-D-Tyr-Arg] | >1000* |
| BL58 | cyc[Arg-Nal-Dap(FP)-Gly-D-Tyr-Arg] | ~1000* |
| BL66 | cyc[(Me)Arg-Nal-Ala-Gly-D-Tyr-Arg] | >1000* |
| BL67 | cyc[Arg-(Me)Nal-Ala-Gly-D-Tyr-Arg] | >1000* |
| BL68 | cyc[Arg-Nal-(Me)Ala-Gly-D-Tyr-Arg] | >1000* |
| BL69 | cyc[Arg-Nal-Ala-(Me)Gly-D-Tyr-Arg] | >1000* |
| BL70 | cyc[Arg-Nal-Ala-Gly-(Me)D-Tyr-Arg] | ~200-300 |
| BL71 | cyc[Arg-Nal-Ala-Gly-D-Tyr-(Me)Arg] | ~1000* |
| BL72 | cyc[(Me)Arg-Nal-Ala-Gly-D-Tyr-(Me)Arg] | >1000* |
| BL73 | cyc[Arg-(Me)Nal-Ala-Gly-D-Tyr-(Me)Arg] | >1000* |
| BL74 | cyc[Arg-Nal-(Me)Ala-Gly-D-Tyr-(Me)Arg] | >1000* |
| BL75 | cyc[Arg-Nal-Ala-(Me)Gly-D-Tyr-(Me)Arg] | >1000* |
| BL76 | cyc[Arg-Nal-Ala-Gly-(Me)D-Tyr-(Me)Arg] | >1000* |
| BL77 | cyc[(Me)Arg-Nal-Ala-Gly-(Me)D-Tyr-Arg] | >1000* |
| BL78 | cyc[Arg-(Me)Nal-Ala-Gly-(Me)D-Tyr-Arg] | >1000* |
| BL79 | cyc[Arg-Nal-(Me)Ala-Gly-(Me)D-Tyr-Arg] | >1000* |
| BL80 | cyc[Arg-Nal-Ala-(Me)Gly-(Me)D-Tyr-Arg] | >1000* |
| BL81 | cyc[(Me)Arg-Nal-Ala-(Me)Gly-D-Tyr-Arg] | >1000* |
| BL82 | cyc[Arg-(Me)Nal-Ala-(Me)Gly-D-Tyr-Arg] | >1000* |
| BL83 | cyc[Arg-Nal-(Me)Ala-(Me)Gly-D-Tyr-Arg] | >1000* |
| BL84 | cyc[(Me)Arg-Nal-(Me)Ala-Gly-D-Tyr-Arg] | >1000* |
| BL85 | cyc[Arg-(Me)Nal-(Me)Ala-Gly-D-Tyr-Arg] | >1000* |
| BL86 | cyc[(Me)Arg-(Me)Nal-Ala-Gly-D-Tyr-Arg] | >1000* |
| BL88 | cyc[Arg-Nal-(Me)Ala-Gly-(Me)D-Tyr-(Me)Arg] | >1000* |
| BL89 | cyc[Arg-(Me)Nal-Ala-Gly-(Me)D-Tyr-(Me)Arg] | >1000* |
| BL92 | cyc[Arg-(Me)Nal-Ala-(Me)Gly-D-Tyr-(Me)Arg] | >1000* |
| BL93 | cyc[(Me)Arg-Nal-Ala-(Me)Gly-D-Tyr-(Me)Arg] | >1000* |
| BL94 | cyc[Arg-(Me)Nal-(Me)Ala-Gly-D-Tyr-(Me)Arg] | >1000* |
| BL96 | cyc[Arg-Nal-(Me)Ala-(Me)Gly-(Me)D-Tyr-Arg] | >1000* |
| BL97 | cyc[Arg-(Me)Nal-Ala-(Me)Gly-(Me)D-Tyr-Arg] | >1000* |
| BL98 | cyc[(Me)Arg-Nal-Ala-(Me)Gly-(Me)D-Tyr-Arg] | >1000* |
| BL99 | cyc[Arg-(Me)Nal-(Me)Ala-Gly-(Me)D-Tyr-Arg] | >1000* |
| BL102 | cyc[Arg-(Me)Nal-(Me)Ala-(Me)Gly-D-Tyr-Arg] | >1000* |
| BL104 | cyc[(Me)Arg-(Me)Nal-Ala-(Me)Gly-D-Tyr-Arg] | >1000* |

These results indicate appreciable loss of binding affinity after N$^\alpha$-methylation of cyclic hexapeptides, although the N-methyl-D-Tyr hexapeptide did not suffer such a significant loss of affinity as most of the other derivatives.

In order to allow more flexibility for the attachment of prosthetic groups for labeling, the introduction of an amino group was investigated by substitution of the Gly residue in CPCR4 for Dap. The results (Table 8) indicate only a moderate loss of affinity following this substitution (note—FP: 2-fluoropropionyl; FB: 4-fluorobenzoyl).

TABLE 8

| Code | Sequence | IC$_{50}$ [nM] |
|---|---|---|
| CPCR4 | cyc[D-Tyr-Arg-Arg-Nal-Gly] | 4 |
| Dap(FP)-8k | cyc[D-Tyr-Arg-Arg-Nal-Dap(FP)] | 140 |
| Dap(FB)-8k | cyc[D-Tyr-Arg-Arg-Nal-Dap(FB)] | 350* |

Other possible modifications of CPCR4 or the other peptides described herein include Nal substitutions with other fluorine-containing aromatic moieties as analogues for the corresponding $^{18}$F-labeled compounds. For example:

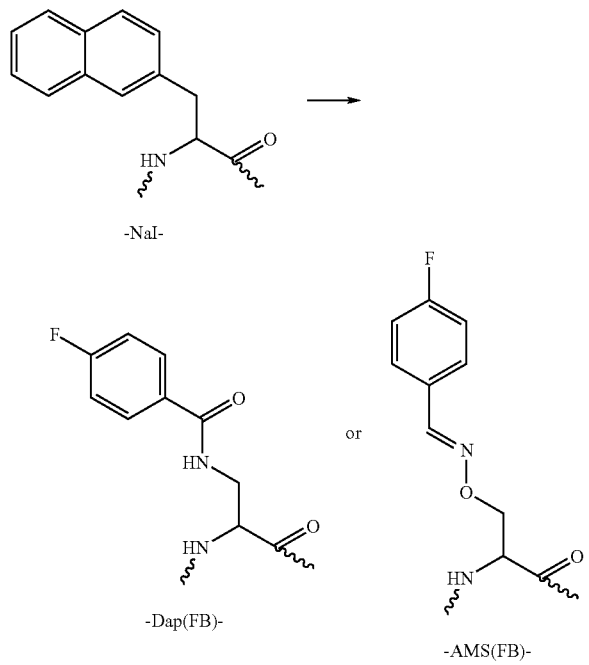

AMS (FB) is an oxime of an aminooxy-serine moiety and 4-fluorobenzaldehyde.

For the development of fluorescent CXCR4 ligands, it is possible to substitute Nal with a fluorescent Dap derivative, such as Dap(NBD) (NBD is 7-nitro-1,2,3-benzoxadiazole). This derivative showed an affinity which was reduced compared to CPCR4, although results from FACS analysis suggest that such a ligand may still be suitable for the investigation of CXCR4 expression by such a technique.

EXAMPLE 3

Multimodal Molecular Imaging of CXCR4 Chemokine Receptor Expression with Peptide-Based Pet Probes and Bioluminescence A key role in metastasis and organ specific homing of tumor cells is attributed to the chemokine receptor CXCR4 and its endogenous ligand SDF-1α. For targeting of CXCR4 expression in vivo we developed a radiolabeled cyclic peptide, CPCR4. $^{125}$I-CPCR4 is the first PET imaging probe that binds with high affinity to CXCR4 (K$_D$=0.4 nM), shows high accumulation in CXCR4 expressing tumors in vivo (5.5% ID/g, 1 h post injection), and allows a clear delineation of CXCR4 positive tumors.

To allow correlation of tumor development with receptor expression and to monitor potential therapeutic interventions using the non-radiolabeled probe by multimodality (bioluminescence and nuclear) imaging, tumor cells have been transduced with luciferase (luc). Lentiviral vectors were constructed containing genes of CXCR4 and luc or otherwise only luc or eGFP as controls. These vectors were successfully used for stable transduction of murine CMS5 fibrosarcoma cells. Surface expression of CXCR4 on CMS5/CXCR4/luc cells was investigated in radioligand binding assays and FACS studies. High affinity and specificity of CPCR4-binding and functional expression of luc were ascertained in cell assays. Transduced cells were injected subcutaneously into nude mice. Animals were analyzed with μ-PET using radiolabeled CPCR4 and bioluminescence (luc)/fluorescence (eGFP) imaging. Ex vivo analysis was performed by autoradiography, bioluminescence measurements and immunohistochemistry. For a better understanding of CPCR4-binding and to design ligands with improved pharmacokinetics, a newly proposed CXCR4 receptor model has been developed and is currently validated by investigating CXCR4 receptor mutants. Based on this computer model, studies on the structure-activity relationship of CPCR4-derivatives are performed for tracer optimization and investigation of other labeling options.

In conclusion, this approach allows imaging of CXCR4 expression in vivo and allows development of enhanced imaging probes for the non-invasive investigation of the metastatic potential of tumors and determination of CXCR4 expression for individualized therapy.

EXAMPLE 4

Preparation and Characterisation of Multimeric Oligopeptide-Based CXCR4 Receptor Binding Compounds 4.1.

A number of cyclic oligopeptide dimers, based on the oligopeptide monomers described herein, were prepared. Such dimers, including the spacer and/or linker groups used in the synthesis thereof, illustrate the general principal for the synthesis of all dimers within the scope of the present invention, as well as higher multimers prepared by incorporation of further cyclic oligopeptides.

Initially, dimers were investigated with the following monomers (denoted Compound A, cyclo[D-Tyr-Orn-Arg-Nal-Gly], and Compound B, cyclo[D-Tyr-(Me)D-Orn-Arg-Nal-Gly]:

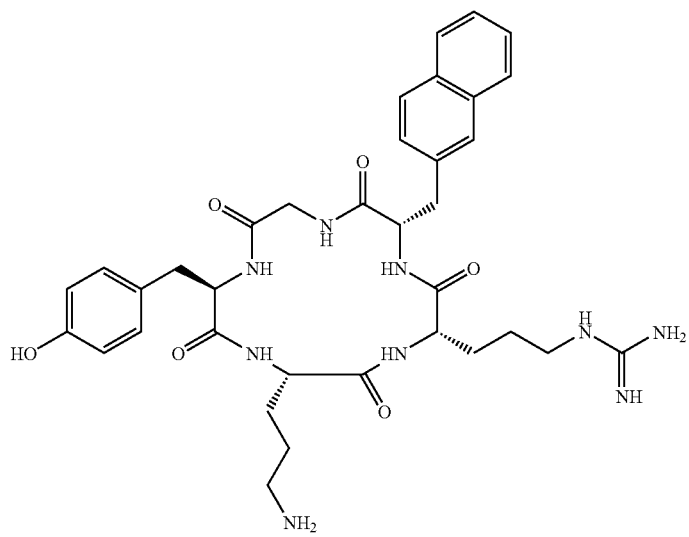
Orn
cyclo[D-Tyr-Orn-Arg-Nal-Gly]
Compound A IC$_{50}$ = 9.1 nM
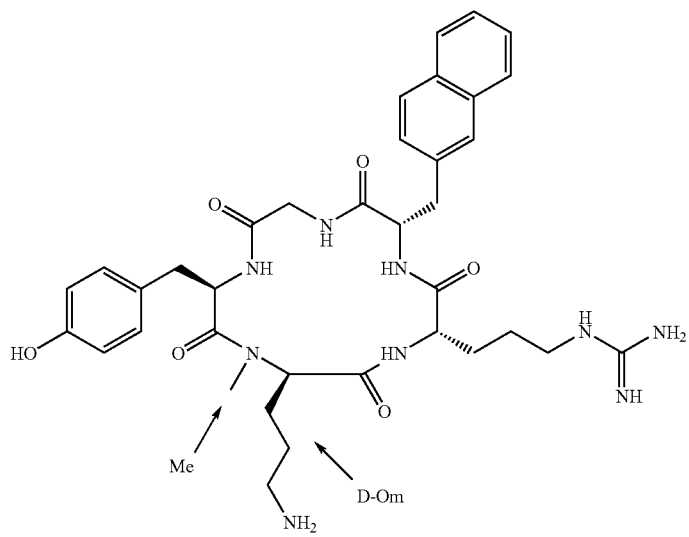
cyclo[D-Tyr-(NMe)-D-Orn-Arg-2-Nal-Gly]
Compound B IC$_{50}$ = 6.15 nM
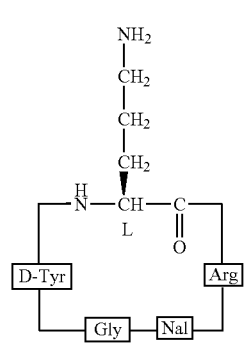
a

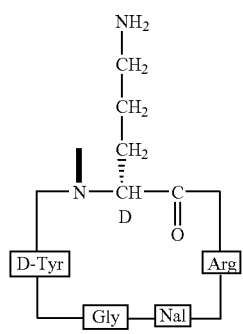
b

Studies on CXCR4 antagonists by Fujii et al. [1] led to the high affinity cyclic pentapeptide cyclo[D-Tyr-Arg-Arg-2-Nal-Gly] (also known as CPCR4 or FC131). The monomeric derivatives of CPCR4, cyclo[D-Tyr-Orn-Arg-2-Nal-Gly] (compound A) and cyclo[D-Tyr-(Me)-D-Orn-Arg-2-Nal-Gly] (compound B) demonstrated an improved affinity (9.1 nM and 6.15±1.2 nM, respectively) compared to CPCR4.

To further improve the affinity of these monomeric CXCR4 ligands, several multimeric CXCR4 ligands have been synthesized. First dimeric peptides of compound A were synthesized via glutaric aldehyde (58.0±4.2 nM) and glutaric acid (4.3±0.3 nM), as illustrated below:

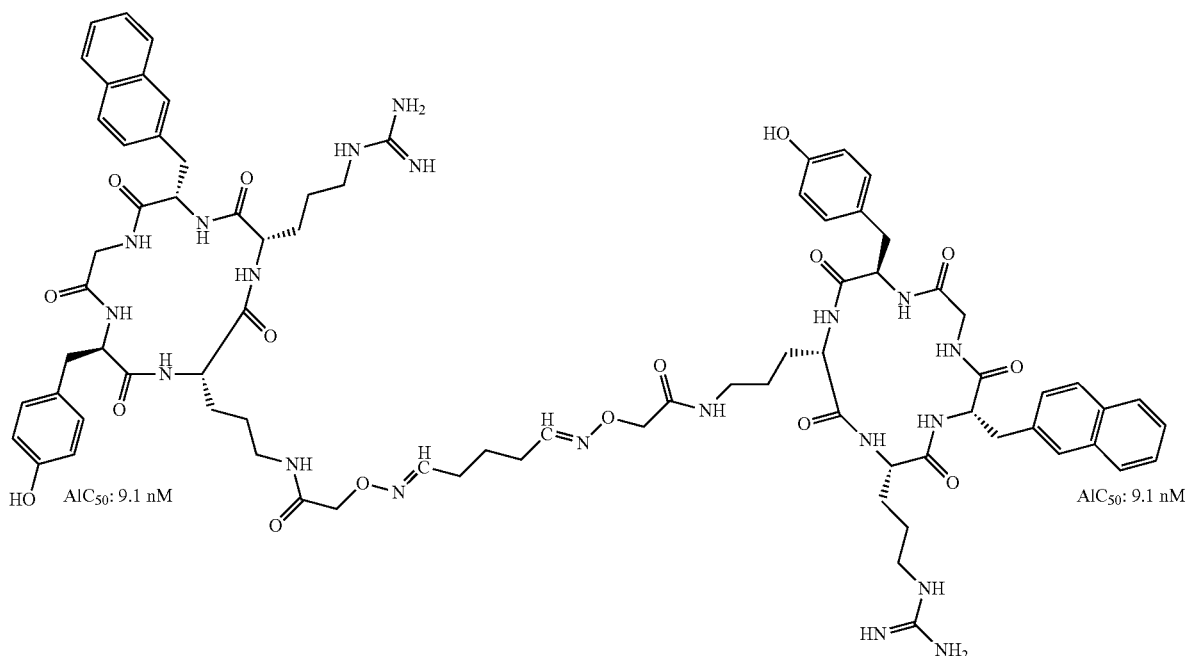

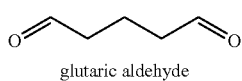
glutaric aldehyde glutaric aldehyde-(cyclo[D-Tyr-Orn(amineoxyacetyl)-Arg-2-Nal-Gly])$_2$/GA1-L-Orn-dimer (A$_2$2) 58.0±4.2 nM

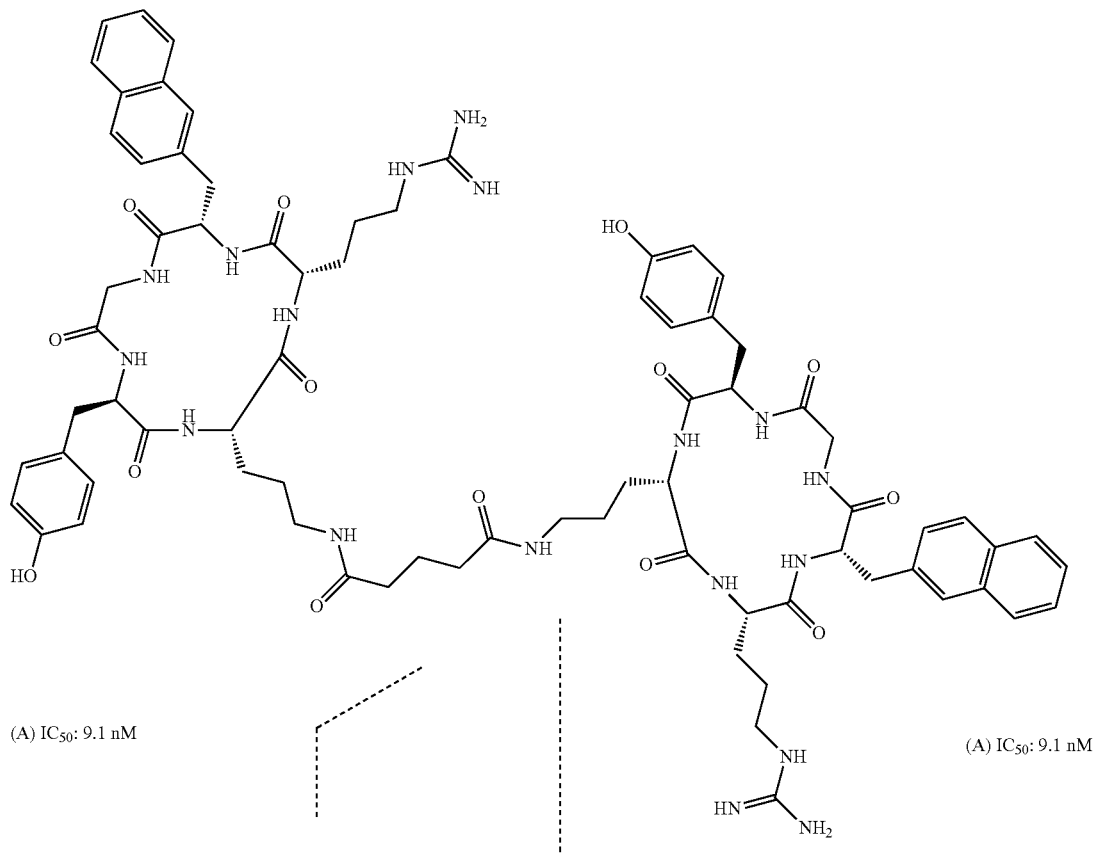

(A) IC$_{50}$: 9.1 nM (A) IC$_{50}$: 9.1 nM glutaric acid-(cyclo[D-Tyr-Orn-Arg-2-Nal-Gly])$_2$ GA-L-Orn-dimer (A$_2$1) 4.3±0.3 nM Note that the gluataric aldehyde was coupled to a pair of ornithine N$^\delta$-aminooxy acetyl derivatives of monomer A, so as to form a di-oxime conjugate.

In general, the dimeric compounds are synthesized by coupling of the amine group of the cyclic peptide (of Orn, Lys or other amino acid with a terminal amine function in its side chain) to the carboxylic acid groups of trifunctional linker (for example Boc-protected aspartic acid, Boc-protected glutamic acid). The Boc group is cleaved off by treatment with TFA. The free amino group can than be used to couple DOTA, DTPA, a fluorescent group, etc. For the synthesis of the subsequent tetramers and oligomers, for example a dimeric compound of the invention (with e.g. Glu or Asp as a linker) is employed, the free amino group of the linker will be used to be coupled to the carboxylic acid groups of another Boc protected Glu or Asp residue. The free amino group can again be coupled to DOTA, DTPA, or a fluorescent group.

Alternatively, this amino group can be used to couple the next dimer to synthesize a "branched tree".

Multimeric compounds can also be synthesized by chemoselective Huisgen reaction, acylation, hydrazone formation, thioethers, etc. These methods have been described in literature.

In terms of the synthetic conditions for the dimers, the above compound employing glutaric acid as linker is illustrative. This was prepared by acylation in solution. For ornithine side chain acylation, cyclized and fully deprotected peptides were stirred with HATU and the corresponding acid in DMF and DIEA as base. The reaction was monitored by ESI-MS. Upon complete conversion, the solvent was evaporated under reduced pressure and injected into the HPLC for purification after dissolution in acetonitrile and water.

The analytical results for all the compounds of the invention described herein are shown in Table 9 below.

The IC50 results reported herein (Table 10 below) for the dimers were determined according to the methods described above.

TABLE 9

| Dimer | calculated exact mass | observed m/z (m + H) | observed m/z (m + 2H) | RT in min (HPLC 10->100%) | HPLC-MS RT in min (HPLC 10->100%) | m/z (m + H) | m/z (m + 2H) |
|---|---|---|---|---|---|---|---|
| Compounds based on monomer containing NMe-D-Orn (i.e. monomer Compound B) | | | | | | | |
| n = 2 | 1484.74 | 1485.6 | 743.7 | 14.84 | — | — | — |
| n = 3 | 1498.75 | 1499.9 | 751.0 | 14.90 | — | — | — |
| n = 4 | 1512.77 | 1513.7 | 757.7 | 15.08 | — | — | — |
| n = 6 | 1540.80 | 1541.8 | 771.7 | 15.17 | — | — | — |
| n = 8 | 1568.83 | 1570.0 | 786.0 | 15.85 | — | — | — |
| n = 11 | 1610.88 | 1611.9 | 806.9 | 16.25 | 9.34 | 1612 | 807 |
| n = 14 | 1652.92 | — | 827.9 | 19.38 | 9.25 | 1654.8 | 827.9 |
| DOTAAhxAsp* | 1999.01 | — | 1000.9 | — | 7.88 | — | 1000.9 |
| InDOTAAhxAsp** | 2111.9 | — | 1056.9 | — | 7.8 | — | 1056.9 |
| DOTAAhxbetaAsp | 2013.03 | — | 1008 | — | 7.81 | — | 1008 |
| InDOTAAhxbetaAsp | 2125.91 | — | 1063.9 | — | 7.84 | — | 1063.9 |
| "Mixed Dimer" (see 4.3 below) | 1499.74 | 1500.9 | — | 15.46 | 10.45 | 1500.8 | — |
| Monomer + Glutaric acid monoamide (see *** below) | 814.41 | 815.5 | — | 12.51 | 8.02 | 815.5 | |
| Compounds based on monomer containing L-Orn (i.e. monomer Compound A) | | | | | | | |
| Linker = Glutaric Acid | 1470.72 | 1471.9 | 737.0 | 15.36 | — | — | — |
| Linker = Aminooxyacetic acid and Glutaraldehyde | 1584.76 | 1585.7 | 793.8 | 15.14 | 8.7 | 1585.7 | 793.8 |
| Compounds based on monomer containing NMe-D-Orn + Gly (see **** below) | | | | | | | |
| n = 1 | 1584.76 | — | 793.8 | — | 8.93 | 1585.5 | 793.8 |
| n = 2 | 1598.78 | — | 800.8 | — | 8.73 | 1599.7 | 800.8 |
| n = 3 | 1612.79 | 1613.6 | 807.8 | 16.52 | 8.19 | 1613.6 | 807.8 |
| DOTAAhxAsp | 2113.05 | — | 1057.9 | — | 7.85 | — | 1057.9 |
| InDOTAAhxAsp | 2225.94 | — | 1113.9 | — | 7.93 | — | 1113.9 |
| DOTAAhxbetaAsp | 2127.07 | — | 1065 | — | 7.86 | — | 1065 |
| InDOTAAhxbetaAsp | 2239.96 | — | 1121 | — | 8.01 | — | 1121 |

NOTES:

*Two monomers B linked via the aspartate diacid of DOTA-Ahx-Asp. DOTA-Ahx-betaAsp is analogous. Corresponding DOTA-containing compounds based on NMe D-Orn + Gly contain the monomers of **** below, linked via the DOTA-Ahx-Asp(or betaAsp) linker.

Two monomers B linked via the aspartate diacid of DOTA-Ahx-Asp, in which the DOTA chelates an In ion. InDOTA-Ahx-betaAsp is analogous. Corresponding InDOTA-containing compounds based on NMe D-Orn + Gly contain the monomers of ** below, linked via the InDOTA-Ahx-Asp(or betaAsp) linker

*** Monomer compound B + glutaric acid monoamide has the structure:

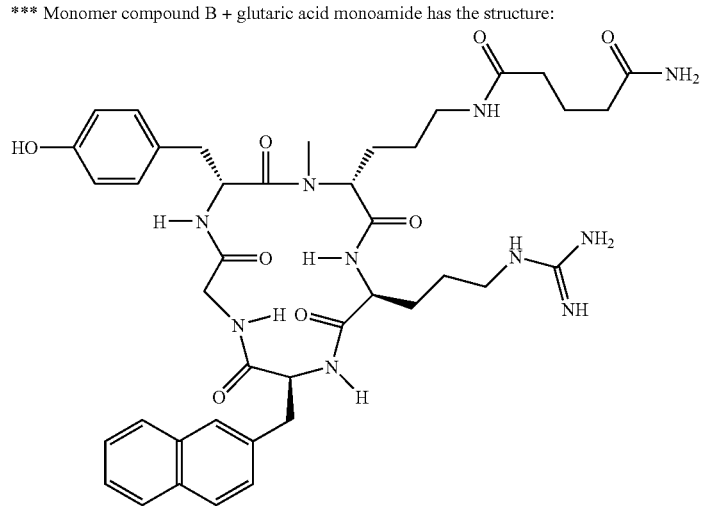

TABLE 9-continued

|  | calculated exact | observed m/z | observed m/z | HPLC-MS | | | |
|---|---|---|---|---|---|---|---|
| Dimer | mass | (m + H) | (m + 2H) | RT in min (HPLC 10->100%) | RT in min (HPLC 10->100%) | m/z (m + H) | m/z (m + 2H) |

**** Compounds based on monomer containing NMe-D-Orn + Gly have the structure:

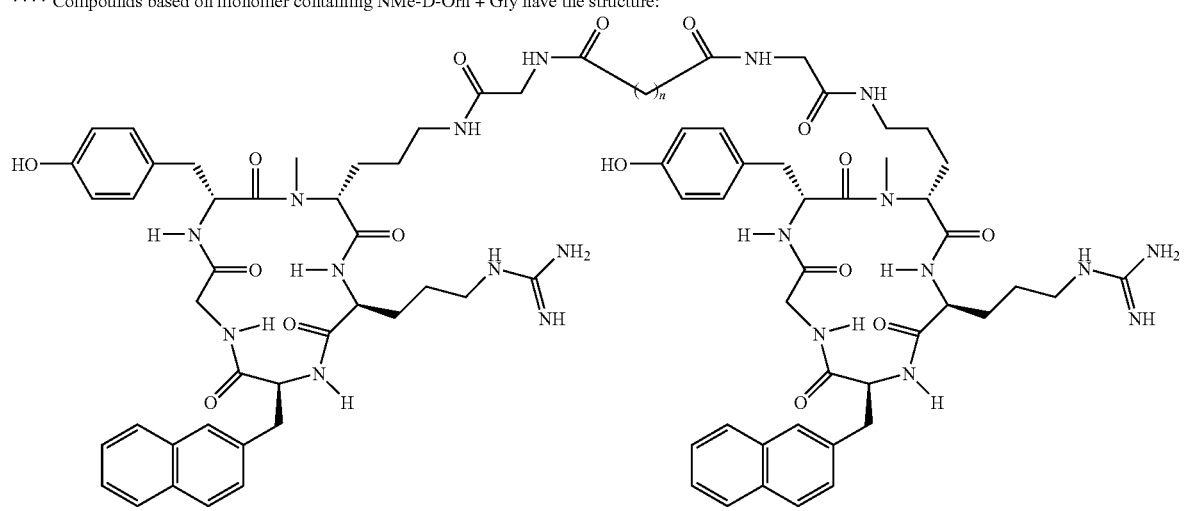

n = 1, 2, 3

TABLE 10

(see notes to Table 9 for further information on reported compounds)

| Dimer | IC50 [nM] Monomer | standard deviation [nM] |
|---|---|---|
| Monomer containing NMe-D-Orn | 6.15 | 1.2 |
| n = 2 | 6.61 | 2.82 |
| n = 3 | 4.28 | 2.3 |
| n = 4 | 3.65 | 1.1 |
| n = 6 | 2.51 | 0.7 |
| n = 8 | 2.26 | 0.7 |
| n = 11 | 11.1 | 3.4 |
| n = 14 | 33.55 | 18.94 |
| DOTAAhxAsp | 92.1 | 6.36 |
| InDOTAAhxAsp | 37.89 | 14.39 |
| DOTAAhxbetaAsp | 43.5 | |
| InDOTAAhxbetaAsp | 45.4 | 40.31 |
| Mixed Dimer | 19.7 | 6.4 |
| Monomer + Glutaric acid monoamide | 66.5 | 4.6 |
| Monomer containing L-Orn | 9.1 | |
| Glutaric Acid | 4.3 | 0.28 |
| Aminooxyacetic acid and Glutaraldehyde | 57.95 | 4.17 |
| Monomer containing NMe-D-Orn + Gly | 2.22 | 0.30 |
| n = 1 | 5.48 | 0.99 |
| n = 2 | 6.29 | 1.86 |
| n = 3 | 13.73 | 2.25 |
| DOTAAhxAsp | 37.97 | 1.84 |
| InDOTAAhxAsp | 13.70 | 2.31 |
| DOTAAhxbetaAsp | 12.26 | 1.66 |
| InDOTAAhxbetaAsp | 22.30 | 5.43 |

4.2.

Multimers with compound B have been synthesised, in this example as dimers. Several dicarboxylic acids have been used as spacers to link the oligopeptides, as illustrated schematically below. It appears that the length of spacer needs to be in an optimum range to reach optimum affinity. For example, suberic acid (HOOC—$(CH_2)_6$—COOH) and sebacic acid (HOOC—$(CH_2)_8$—COOH) were the most optimal spacers ($IC_{50}$=2.51±0.7 nM and 2.12±0.9 nM, respectively). Using shorter or longer spacers such as glutaric acid (HOOC—$(CH_2)_3$—COOH), adipic acid (HOOC—$(CH_2)_4$—COOH), or tridecanedioic acid (HOOC—$(CH_2)_{11}$—COOH) resulted in a lower affinity (4.28±2.3 nM, 4.42 nM, and 11.1±3.4 nM respectively).

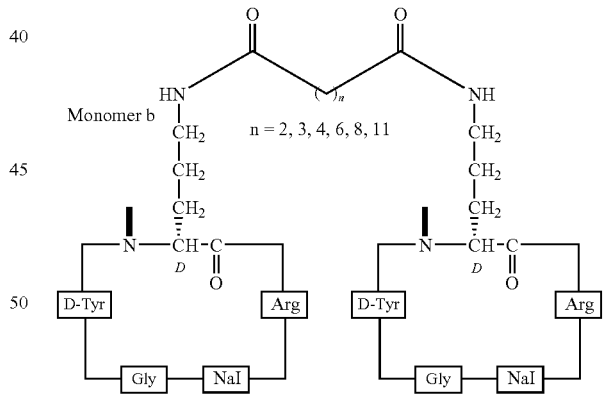

The binding affinity results for dimers of compound B with varying lengths of linker/spacer (the value n referring to the number of methylene groups in the schematic above) are reported in Table 10.

4.3.

A dimer consisting of compound B with a non-binding cyclic pentapeptide, and employing glutaric acid as a spacer ('Mixed Dimer', illustrated below), was found to have a lower affinity compared to its analogue consisting of two B units ($B_21$). This indicates that multimeric CXCR4 ligands have improved affinity compared to their monomeric counterparts, and that the higher binding affinity of a dimer such as $B_21$ is not due to differences in size, charge or shape compared to the monomer (the heterodimer confirms this).

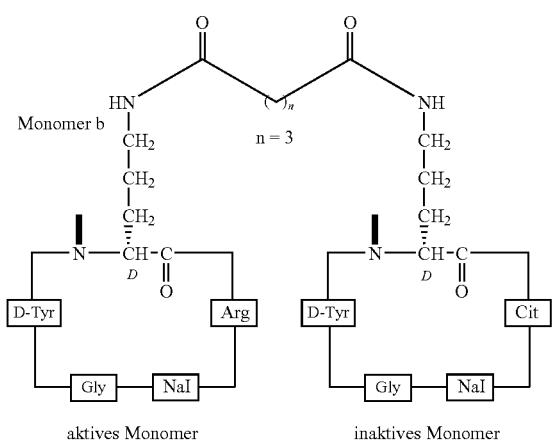

aktives Monomer    inaktives Monomer

The results were as follows: Monomer B alone (i.e. left hand monomer in above schematic) IC$_{50}$=6.15 nM; 'inactive', citrulline-containing monomer alone (i.e. right hand monomer in above schematic) IC$_{50}$>10 mM; and dimer, consisting of monomer B and the inactive monomer: IC$_{50}$=19.5±8.9.

The homodimer B$_2$1 is shown below:

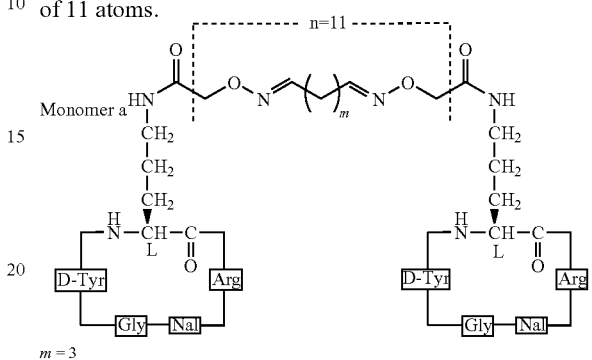

$m = 3$ dimer consisting of cyclo[D-Tyr-Orn-Arg-2-Nal-Gly] monomers linked via a glutaric dialdehyde spacer which binds to the amino-oxyacetyl-groups connected to the Orn-side chains was prepared. The entire linker (spacer), without the two carbonyl groups joined to the Orn delta-amino groups, consists of 11 atoms. In the lower schematic (monomer B), a dimer consisting of cyclo[D-Tyr-Orn-Arg-2-Nal-Gly] monomers linked via a tridecanedioic acid (HOOC—(CH$_2$)$_{11}$COOH) spacer which binds directly to the Orn-side chains. This spacer—without the two carbonyl groups—also consists of 11 atoms.

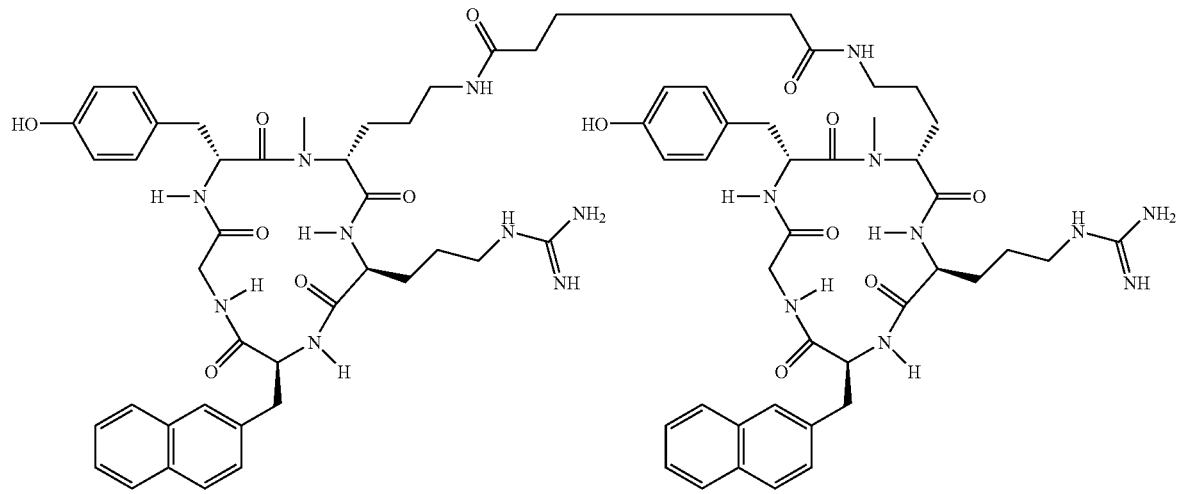

glutaric acid (cyclo[D-Tyr-NMe-D-Orn-R-Nal-G])$_2$; IC$_{50}$: 4.28 ± 2.3 nM depicted above
glutaric acid (cyclo[D-Tyr-Orn-R-Nal-G])$_2$; IC$_{50}$: 4.3 ± 0.3 nM From these results it can be concluded that the affinity of CXCR4 ligands can be improved by multimerization, e.g. dimerization. Affinity of the dimeric compounds depends at least upon the spacer length (4.2 above) and the structure of the spacer, as will be illustrated below (4.4).

4.4.

For example, the dimeric peptide glutaric aldehyde-(cyclo [D-Tyr-Orn(amineoxyacetyl)-Arg-2-Nal-Gly])$_2$ (A$_2$2) has a significantly lower affinity (58.0±4.2 nM) compared to the cyclo[D-Tyr-(Me)-D-Orn-Arg-2-Nal-Gly] dimer linked with a tridecanedioic acid (HOOC—(CH$_2$)$_{11}$COOH) spacer (see below). Both spacers consist of the same number of atoms and only differ in the structure of the spacer. The significant difference in the affinity of both compounds, as expressed by the IC$_{50}$ value in the competition assay, can not be explained by the different monomers used (as illustrated above, monomer A and monomer B with either L-Orn or NMe-D-Orn in the peptide chain, have very similar affinities). This difference can only be explained by the different structure of the spacer. As shown below, in the upper schematic (monomer A), a -continued

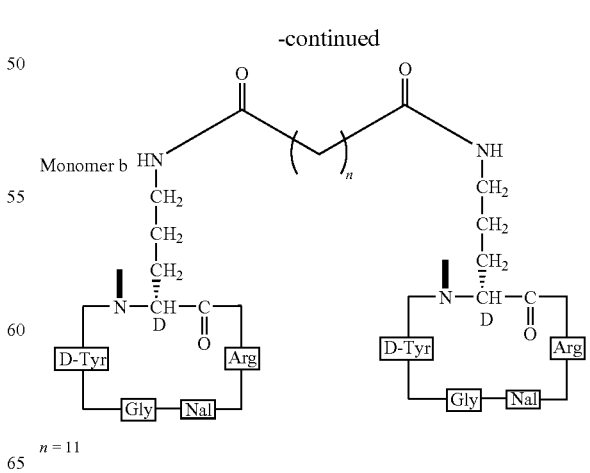

$n = 11$ 4.5.

In addition, it has been demonstrated that introduction of a cyclic peptide with no affinity for CXCR4 generated by exchange of Arg versus Cit in monomer B, i.e. cyclo[D-Tyr-(Me)-D-Orn-Cit-2-Nal-Gly] into a dimer with compound/monomer A shows a similar or only fractionally lower affinity than the corresponding high affinity monomer alone and the corresponding homo-dimer ($A_2$1) (see below).

cyclo[D-Tyr-Orn-R-Nal-G]
$IC_{50}$: 9.1 nM (A) $IC_{50}$ = 9.1 nM

D-Tyr-NMe-D-Orn-Cit-Nal-Gyl $IC_{50}$ > 1 mM

Mixed Dimer ($A_2$3) $IC_{50}$ = 9.7 nM

The homo-dimer, $A_2$1, is illustrated in 4.1 above, and has an 1050 of 4.3±0.3 nM.

4.6.

Thus, multimeric compounds, such as e.g. dimers, trimers, tetramers and greater oligomers (dendrimers) can be generated with high affinity for the CXCR4 receptor. These multimers are synthesized using monomeric cyclic pentapeptides coupled to different spacers and/or linker moieties. The spacer will be linked to amino acids in the cyclic peptides, such as Orn, D-Om or NMe-D-Orn. A variety of spacers can be used, e.g. dicarboxylic acids, amino acids (lysine, glutamic acid) and amino acid chains (small peptides), polyethylene glycol chains (PEG) or alkynes. These linkers have multifunctional groups, which allows for coupling of a) multiple monomeric-peptide-linker units and b) signalling units, e.g. radiolabeled groups, such as radiometallated chelators or prothetic groups, or fluorescent groups to one complex construct.

A number of such approaches are shown schematically below by way of example:

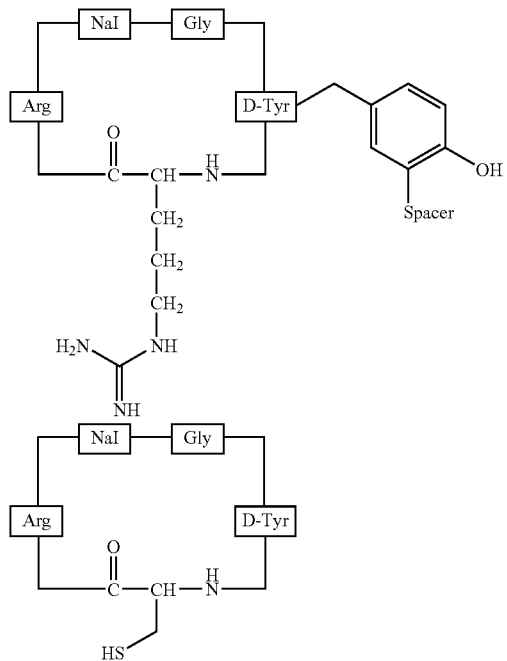

The above schematic shows different strategies for coupling of a spacer to the cyclic peptides. At the top, modified tyrosine is used to couple the spacer. In addition, Tyr can be O-alkylated to directly conjugate the spacer to unmodified Tyr. In addition, other amino acids, such as Cys, can be introduced to offer functional groups for conjugation. Formation of maleimides or thioethers, and especially reaction with alpha-haloketones and alpha-haloamides, are suitable modifications to introduce a spacer at this amino acid (bottom example in the schematic).

4.7.

A number of carboxylic acid-based spacers are shown below:

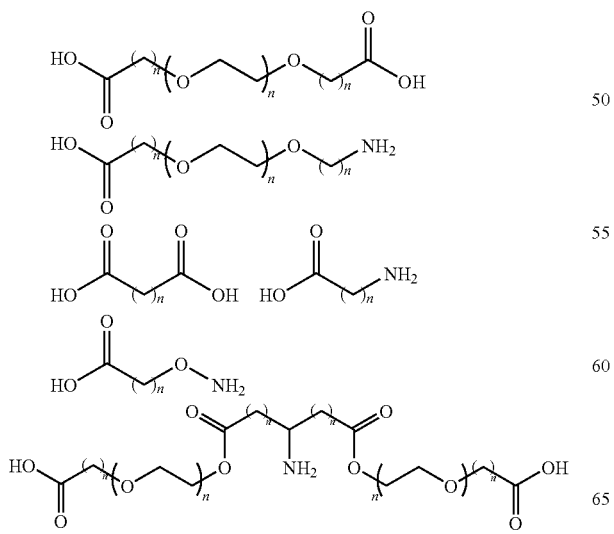

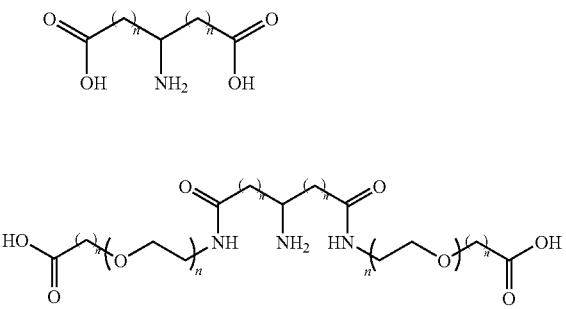

In addition to these examples of spacer and/or linker groups, further spacers, i.e. spacers for alkylation, generated by formal exchange of one or two of the carboxylic acid residues by alcohols or halogens, are suitable linkers or spacers. Amino acid chains, or small linear peptides, are also possible linkers and/or spacers.

4.8.

It has also been found that, surprisingly, large bulky groups directly connected to the side chain of Urn in the cyclic oligopeptides will not significantly affect the affinity, e.g. as shown in the following example monomers.

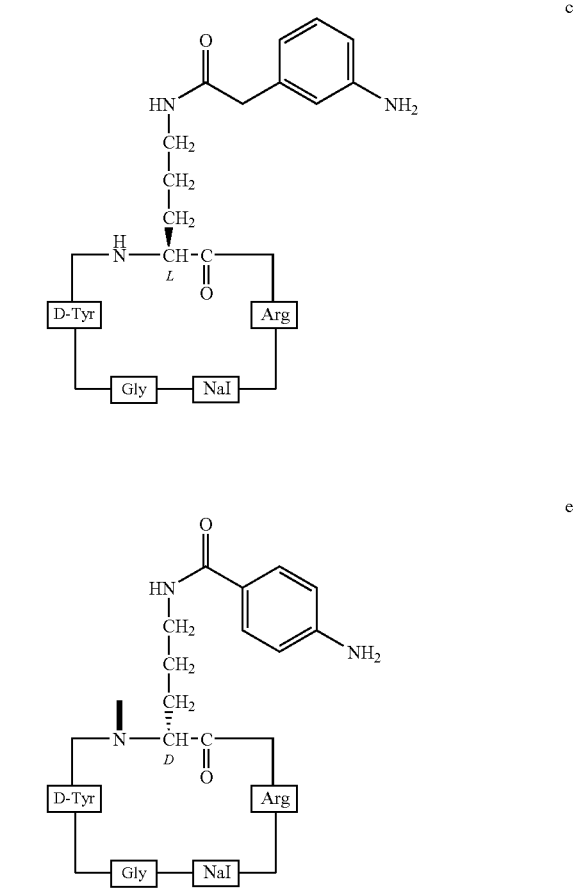

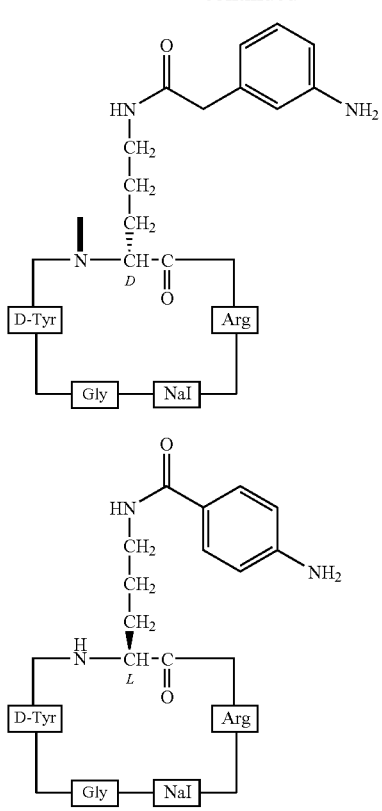

This finding opens up additional possibilities for combining the cyclic oligopeptides into dimers and multimers by means of linkers and spacers containing a variety of functional groups, not necessarily limited in size or bulk, for attachment of other oligopeptides, labels, cytotoxic moieties and other groups to alter the pharmacokinetic and pharmacodynamic properties of the conjugates.

4.8.

Figure 5:
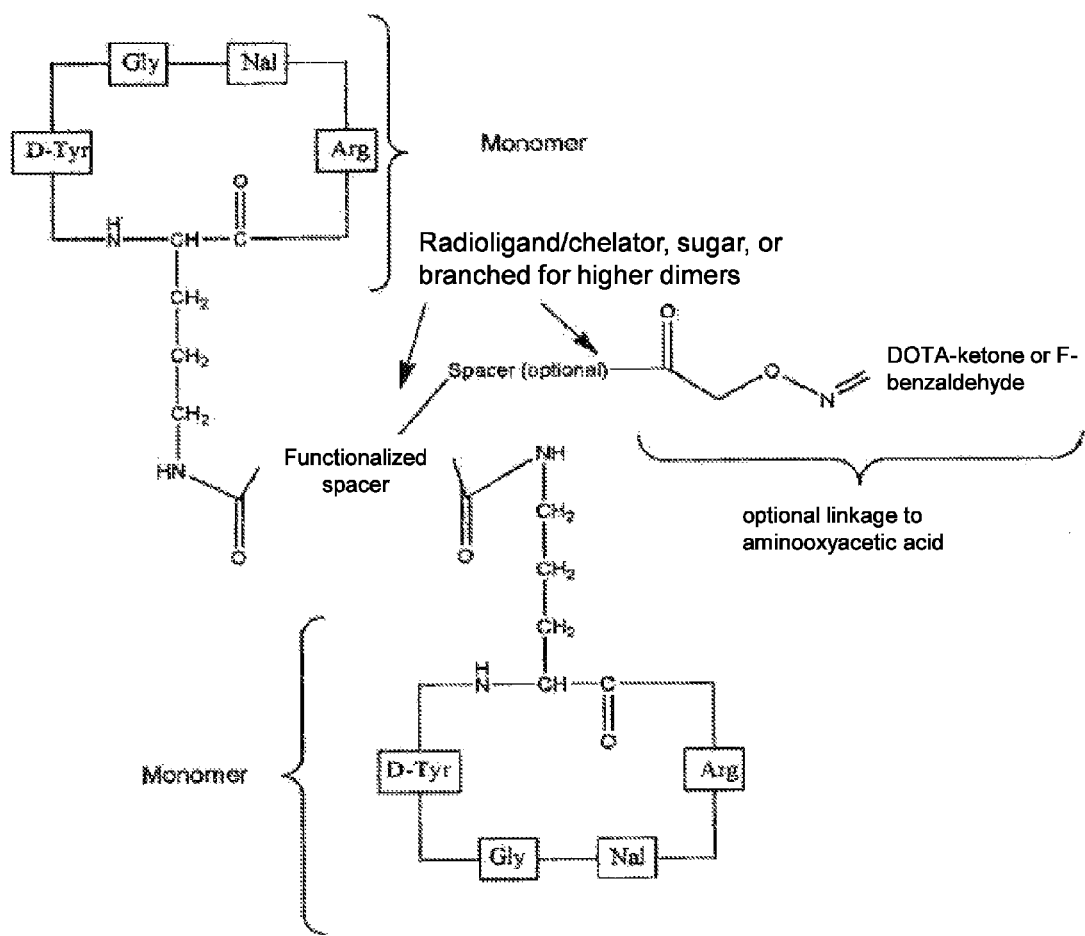
FIG. 5 shows schematically a multimeric compound of the present invention bearing a detectable label.

In conclusion, constructs as illustrated schematically in FIG. 5 are expected to have significant impact for therapeutic and diagnostic interventions in conditions in which the CXCR4 receptor is implicated. The construct of FIG. 5 comprises a homo-dimer of two relatively high affinity monomers, joined together by a linker group. The linker group is at least trifunctional, and allows for the coupling, via an optional spacer group, of a radiolabel, either in the form a $^{18}$F-bearing substituent, or a radiometal in complex with a chelating agent, such as DOTA.

It will be appreciated that multimerisation can occur by coupling of multiple peptide or peptide-spacer units to a multifunctional moiety (i.e. the linker), which is also used for coupling of the signalling unit/detectable label. It will further be readily understood that the structure of the linker can be very flexible, thus can also consist of e.g. a sugar, where the OH-functions are alkylated, or an oligo- or polyamine or oligo- or poly-aminooxy-functionalized molecule, peptide or resin.

Multimers may be prepared by coupling of multiple peptide or peptide-spacer units to a single linker or by the coupling of multiple linkers. Thus, in an embodiment, three trifunctional linkers are joined in series, together with four oligopeptide units and a chelating agent (DOTA), to form the construct (P1-spacer)$_2$-Linker-Linker(DOTA)-Linker-(spacer-P1)$_2$.

With multifunctional linkers, such as oligopeptides or polyamines, it will be understood that, not only may multiple cyclic oligopeptides be joined to the same linker, together with detectable labels as necessary, but multiple linkers may be couple to each other. Thus, in another embodiment, multiple linkers are coupled, each typically bearing 2 or more cyclic oligopeptide moieties. Thus, a dimer may be converted to a tetramer by coupling between the two linker groups. Such linker-linker coupling may be by means of a further spacer group. It will be appreciated that higher multimers, such as dendrimers, may be prepared by such a multiplicative synthetic approach. Such multimers offer the ability to achieve significantly higher binding affinity and selectivity, and furthermore offer significant opportunities for the attachment of additional groups for modifying the properties of the compound.

The results presented herein in relation to novel cyclic oligopeptide monomers are illustrative of the results which may be obtained with dimers or higher multimers containing such oligopeptides. In addition, dimers according to the present invention may contain known cyclic oligopeptide CXCR4 ligands and it has been demonstrated herein that surprising improvements in CXCR4 receptor affinity may be obtained, even when employing relatively weak-binding oligopeptides.

It will further be appreciated that the dimer results described herein are illustrative of the results which would be expected with trimers and higher multimers of the cyclic oligopeptides.

EXAMPLE 5

Preparation of a Conjugate Between a CXCR4-Binding Cyclic Oligopeptide and a Chelating Agent The person of ordinary skill in the art would readily be able to prepare a construct or conjugate consisting of a multimer of cyclic oligopeptides according to the present invention, a suitable spacer moiety (preferably one of the linker moieties described herein), and a chelator or other moiety suitable for complexation of a radiometal. Typically, as described in numerous publications in recent years, DOTA, for example, is coupled to a linker-bearing, fully protected oligopeptide, either using a tri-protected (e.g. tri-tert-butyl—protected) DOTA using standard activation procedures, or using pre-activated species of DOTA, for example mono-, di-, tri- or tetra N-succinimidyl esters or 4-nitrophenyl esters of DOTA. Alternatively, standard peptide coupling conditions can be used to achieve this goal.

Similarly, other chelators/complexation moieties, such as TETA or DTPA, can be coupled. DTPA may also be coupled using the cyclic bis-anhydride. Obviously, the chelator may also be pre-coupled to the spacer, thus resulting in the formation of the peptide-spacer bond in the final step.

As examples of a suitable approach, the compounds based on the DOTA-Ahx-Asp linker-chelator conjugate described herein may be referred to. These compounds show an ability to chelate metals of relevance to radiopharmaeuticals (as shown in the results with the InDOTA analogues), yet still show a strong ability to bind to the target CXCR4 receptor (Table 10).

The coupling of chelators or complexation agents can also be achieved by a person of ordinary skill in the art using the well-described coupling procedures established in the radiopharmaceutical field. Other coupling routes such as oxime or hydrazone formation, as well as other selective methods, such as the reaction of thiols and maleimides, may be used to reach similar results.

The foregoing Examples are intended to illustrate specific embodiments of the present invention and are not intended to limit the scope thereof, the scope being defined by the appended claims. All documents cited herein are incorporated herein by reference in their entirety.

REFERENCES

1. Fujii, N., et al., Molecular-size reduction of a potent CXCR4-chemokine antagonist using orthogonal combination of conformation- and sequence-based libraries. Angew Chem Int Ed Engl, 2003. 42(28): p. 3251-3.
2. Haubner, R., et al., Radiolabeled alpha(v) beta3 integrin antagonists: a new class of tracers for tumor targeting. J Nucl Med, 1999. 40(6): p. 1061-71.
3. Gansbacher, B., et al., Retroviral vector-mediated gamma-interferon gene transfer into tumor cells generates potent and long lasting antitumor immunity. Cancer Res, 1990. 50(24): p. 7820-5.
4. DuBridge, R. B., et al., Analysis of mutation in human cells by using an Epstein-Barr virus shuttle system. Mol Cell Biol, 1987. 7(1): p. 379-87.
5. Loetscher, M., et al., Cloning of a human seven-transmembrane domain receptor, LESTR, that is highly expressed in leukocytes. J Biol Chem, 1994. 269(1): p. 232-7.
6. Anton, M., et al., Use of the norepinephrine transporter as a reporter gene for non-invasive imaging of genetically modified cells. J Gene Med, 2004. 6(1): p. 119-26.
7. Fan, G. H., et al., Hsc/Hsp70 interacting protein (hip) associates with CXCR2 and regulates the receptor signaling and trafficking. J Biol Chem, 2002. 277(8): p. 6590-7.
8. Forster, R., et al., Intracellular and surface expression of the HIV-1 coreceptor CXCR4/fusin on various leukocyte subsets: rapid internalization and recycling upon activation. J Immunol, 1998. 160(3): p. 1522-31.
9. Gupta, S. K., et al., Pharmacological evidence for complex and multiple site interaction of CXCR4 with SDF-1alpha: implications for development of selective CXCR4 antagonists. Immunol Lett, 2001. 78(1): p. 29-34.
10. Hesselgesser, J., et al., Identification and characterization of the CXCR4 chemokine receptor in human T cell lines: ligand binding, biological activity, and HIV-1 infectivity. J Immunol, 1998. 160(2): p. 877-83.
11. Balkwill, F., Nature Reviews, 2004, 4: p. 540-550
12. Tamamura H et al., J Med Chem, 2005, 48: p. 3280-9
13 Fields G B, Noble R L. Solid phase peptide synthesis utilizing 9-fluorenylmethoxycarbonyl amino acids. Int. J. Pept. Protein Res. 1990; 35: p. 161-214.
14 Biron E, Chatterjee J, Kessler H. Optimized Selective N-Methylation of Peptides on Solid Support. J. Peptide Sci. 2006; 12: p. 213-219.

The invention claimed is:

1. A compound, or a pharmaceutically acceptable salt or ester thereof, comprising the structure:

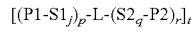

wherein:
P1 and P2, which may be the same or different, are cyclic oligopeptide moieties, at least one of P1 and P2 having the motif B-Arg or B-(Me)Arg within the cyclic moiety, wherein B is an Nα-methyl derivative of a basic amino acid, or an Nα-methyl derivative of phenylalanine;
S1 and S2 are spacer groups, which may be the same or different;
L is a linker moiety containing at least two functional groups for attachment of the cyclic oliqopeptides or spacer groups;
j and q are independently 0 or 1;
p and r are independently integers of 1 or more; and
t is an integer of 1 or more,
provided that, when t, p or r is greater than 1, the cyclic oliqopeptide moiety, spacer group and/or the value of j or q may be the same or different between the multiple (P1-S1$_j$) moieties or multiple (S2$_q$-P2) moieties.

2. A compound, or a pharmaceutically acceptable salt or ester thereof, comprising the structure:

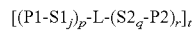

wherein:
S1 and S2 are spacer groups, which may be the same or different;
L is a linker moiety containing at least two functional groups for attachment of the cyclic oliqopeptides or spacer groups;
j and q are independently 0 or 1;
p and r are independently integers of 1 or more; and
t is an integer of 1 or more,
P1 and P2, which may be the same or different, are cyclic oliqopeptide moieties, at least one of P1 and P2 is selected from cyclic oligopeptides having the sequence:

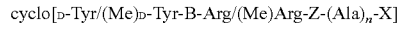

wherein B is Orn or D-Orn, the ornithine residue being substituted at Nα with one or two groups selected from fluorobenzoyl (FB), fluoropropionyl (FP), acetyl (Ac), amido (Am), Me, 1-naphthylmethyl (N1), 2-naphthylmethyl (N2), benzyl (Bz) and acyl spacer moieties, wherein the acyl spacer moiety is an acyl group containing a chain of 1-14 carbons, optionally interrupted by heteroatoms, and having a nucleophilic functional group at its end distal to the ornithine Nα;
Z is an amino acid containing an aromatic group in its side chain;
n is 1 or 0, provided that n is 1 only when the preceding four amino acids in the cyclic moiety sequence are D-Tyr/(Me)-D-Tyr-Arq-Arq-Nal, Nal being L-3-(2-naphthyl)alanine; and
X is selected from Gly, (Me)Gly, Ala, Dap (diaminopropionic acid), Dap(FP) ((N-fluoropropionyl)-diaminopropionic acid), Dab (diaminobutyric acid), Dab(FP) ((N-fluoropropionyl)-diaminobutyric acid), Dab(FB) ((N-fluorobenzoyl)-diaminobutyric acid) and Dap(FB) ((N-fluorobenzoyl)-diaminopropionic acid);
provided that, when t, p or r is greater than 1, the cyclic oligopeptide moiety, spacer group and/or the value of j or q may be the same or different between the multiple (P1-S1$_j$) moieties or multiple (S2$_q$-P2) moieties.

* * * * *